United States Patent

Schwark et al.

[11] Patent Number: 6,005,010
[45] Date of Patent: Dec. 21, 1999

[54] PHENYL-SUBSTITUTED ALKENYLCARBOXYLIC ACID GUANIDIDES, PROCESS FOR THEIR PREPARATION, THEIR USE AS A MEDICAMENT OR DIAGNOSTIC, AND MEDICAMENT CONTAINING THEM

[75] Inventors: Jan-Robert Schwark, Frankfurt; Joachim Brendel, Bad Vilbel; Heinz-Werner Kleemann, Bischofsheim; Hans Jochen Lang, Hofheim; Andreas Weichert, Egelsbach; Hans-Willi Jansen, Niedernhausen; Wolfgang Scholz, Eschborn, all of Germany

[73] Assignee: Hoechst Aktiengesellschaft, Frankfurt am Main, Germany

[21] Appl. No.: 08/915,329

[22] Filed: Aug. 20, 1997

[30] Foreign Application Priority Data

Aug. 22, 1996 [DE] Germany .................. 196 33 966

[51] Int. Cl.⁶ .................................. A61K 31/165
[52] U.S. Cl. .................. 514/616; 514/346; 514/821; 514/866; 514/921; 546/291; 564/153; 564/154; 564/155; 564/156
[58] Field of Search ................. 564/153, 154, 564/155, 156; 546/291; 514/346, 616, 821, 866, 921

[56] References Cited

U.S. PATENT DOCUMENTS 4,544,670  10/1985  Studt et al. .................. 514/617

FOREIGN PATENT DOCUMENTS 640 587    3/1995   European Pat. Off. .
44 21 536  12/1995  Germany .
WO 84/00875 3/1984  WIPO .

OTHER PUBLICATIONS

Duff et al.; "Amiloride: Antiarrhythmic and Electrophysiologic Actions in Patients with Inducible Sustained Ventricular Tachycardia", Circulation, vol. 79, No. 6, pp. 1257–1263, Jun. 1989.

A. Schomig et al.; "Inhibition of $Na^+/H^+$ Exchange Suppresses Noradrenaline Release and Arrhythmias in the Ischemic Rat Heart", Eur. Heart J. 9(suppl. 1) p. 167 (1988), Book of Abstracts.

Derwent Abstract of EP 640 587.

Derwent Abstract of DE 44 21 536.

*Primary Examiner*—Peter G. O'Sullivan
*Attorney, Agent, or Firm*—Finnegan, Henderson, Farabow, Garrett & Dunner, L.L.P.

[57] ABSTRACT

Compounds of the formula

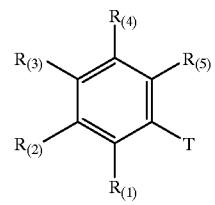

where T is

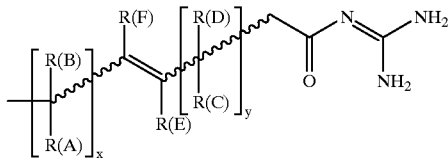

and R(A), R(B), R(C), R(D), R(E), R(F), x and y have the meanings indicated in the claims, and their pharmaceutically acceptable salts are effective inhibitors of the cellular sodium-proton antiporter ($Na^+/H^+$ exchanger). These compounds are therefore outstandingly suitable for treatment of all illnesses which are to be attributed to increased $Na^+/H^+$ exchange.

21 Claims, No Drawings

PHENYL-SUBSTITUTED ALKENYLCARBOXYLIC ACID GUANIDIDES, PROCESS FOR THEIR PREPARATION, THEIR USE AS A MEDICAMENT OR DIAGNOSTIC, AND MEDICAMENT CONTAINING THEM

The invention relates to phenyl-substituted alkenylcarboxylic acid guanidides of the formula I

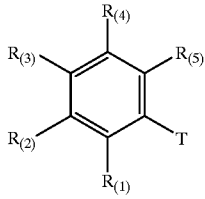

in which:
T is

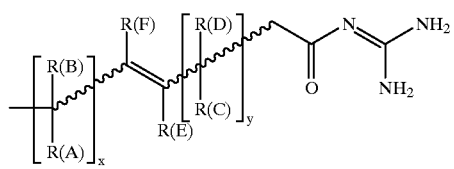

R(A) is hydrogen, F, Cl, Br, I, CN, OH, OR(6), $(C_1-C_4)$-alkyl, $O_r(CH_2)_aC_bF_{2b+1}$, $(C_3-C_8)$-cycloalkyl or NR(7)R(8);
r is zero or 1;
a is zero, 1, 2, 3 or 4;
b is 1, 2, 3 or 4;
R(6) is $(C_1-C_4)$-alkyl, $(C_1-C_4)$-perfluoroalkyl, $(C_3-C_6)$-alkenyl, $(C_3-C_8)$-cycloalkyl, phenyl or benzyl, the phenyl nucleus being unsubstituted or substituted by 1–3 substituents selected from the group consisting of F, Cl, $CF_3$, methyl, methoxy and NR(9)R(10);
R(9) and R(10) are H, $(C_1-C_4)$-alkyl or $(C_1-C_4)$-perfluoroalkyl;
R(7) and R(8) independently of one another are defined as R(6);
or
R(7) and R(8) together are 4 or 5 methylene groups, of which one $CH_2$ group can be replaced by oxygen, sulfur, NH, N—$CH_3$ or N-benzyl;
R(B), R(C) and R(D) independently are defined as R(A);
x is zero, 1 or 2;
y is zero, 1 or 2;
R(F) is hydrogen, F, Cl, Br, I, CN, OR(12), $(C_1-C_8)$-alkyl, $O_p(CH_2)_fC_gF_{2g+1}$, $(C_3-C_8)$-cycloalkyl or $(C_1-C_9)$-heteroaryl;
p is zero or 1;
f is zero, 1, 2, 3 or 4;
g is 1, 2, 3, 4, 5, 6, 7 or 8;
R(12) is $(C_1-C_8)$-alkyl, $(C_1-C_4)$-perfluoroalkyl, $(C_3-C_8)$-alkenyl, $(C_3-C_8)$-cycloalkyl, phenyl or benzyl, the phenyl nucleus being unsubstituted or substituted by 1–3 substituents selected from the group consisting of F, Cl, $CF_3$, methyl, methoxy and NR(13)R(14); R(13) and R(14) are H, $(C_1-C_4)$-alkyl or $(C_1-C_4)$-perfluoroalkyl;
R(E) is defined as R(F);
R(1) is defined as T;
or
R(1) is hydrogen, $-O_kC_mH_{2m+1}$, $-O_n(CH_2)_pC_qF_{2q+1}$, F, Cl, Br, I, CN, $-(C=O)-N=C(NH_2)_2$, $-SO_rR(17)$, $-SO_{r2}NR(31)R(32)$, $-O_u(CH_2)_vC_6H_5$, $-O_{u2}-(C_1-C_9)$-heteroaryl or $-S_{u2}-(C_1-C_9)$-heteroaryl;
k is zero or 1;
m is zero, 1, 2, 3, 4, 5, 6, 7 or 8;
n is zero or 1;
p is zero, 1, 2, 3 or 4;
q is 1, 2, 3, 4, 5, 6, 7 or 8;
r is zero, 1, 2;
r2 is zero, 1 or 2;
R(31) and R(32) independently of one another are hydrogen, $(C_1-C_8)$-alkyl or $(C_1-C_8)$-perfluoroalkyl;
or
R(31) and R(32) are together 4 or 5 methylene groups, one of which can be substituted by oxygen, S, NH, N—$CH_3$ or N-benzyl;
R(17) is $(C_1-C_8)$-alkyl;
u is zero or 1;
u2 is zero or 1;
v is zero, 1, 2, 3 or 4;
the phenyl nucleus being unsubstituted or substituted by 1–3 substituents selected from the group consisting of F, Cl, $CF_3$, methyl, methoxy, $-(CH_2)_wNR(21)R(22)$, NR(18)R(19) and $(C_1-C_9)$-heteroaryl;
R(18), R(19), R(21) and R(22) independently of one another are $(C_1-C_4)$-alkyl or $(C_1-C_4)$-perfluoroalkyl;
w is 1, 2, 3 or 4; the heterocycle of the $(C_1-C_9)$-heteroaryl is unsubstituted or substituted by 1–3 substituents selected from the group consisting of F, Cl, $CF_3$, methyl and methoxy;
R(2), R(3), R(4) and R(5) independently of one another are defined as R(1),
or
R(1) and R(2) or R(2) and R(3) in each case together are —CH—CH=CH—CH—, which is unsubstituted or is substituted by 1–3 substituents selected from the group consisting of F, Cl, $CF_3$, methyl, methoxy, $-(CH_2)_{w2}NR(24)R(25)$ and NR(26)R(27);
R(24), R(25), R(26) and R(27) are H, $(C_1-C_4)$-alkyl or $(C_1-C_4)$-perfluoroalkyl;
w2 is 1, 2, 3 or 4;
the radical T being present in the molecule at least twice, but only three times at most; and their pharmaceutically acceptable salts.

Preferred compounds of the formula I are those in which:
T is

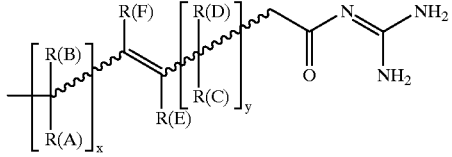

R(A) is hydrogen, F, Cl, CN, OH, OR(6), $(C_1-C_4)$-alkyl, $O_r(CH_2)_aC_bF_{2b+1}$, $(C_3-C_8)$-cycloalkyl or NR(7)R(8);
r is zero or 1;
a is zero, 1 or 2;
b is zero, 1, 2, 3 or 4;
R(6) is $(C_1-C_4)$-alkyl, $(C_1-C_4)$-perfluoroalkyl, phenyl or benzyl, the phenyl nucleus being unsubstituted or substituted by 1–3 substituents selected from the group consisting of F, Cl, $CF_3$, methyl, methoxy and NR(9)R(10);
    R(9) and R(10) independently of one another are H, $CH_3$ or $CF_3$;
    R(7) and R(8) independently of one another are defined as R(6);
or
    R(7) and R(8) together are 4 or 5 methylene groups, of which one $CH_2$ group can be replaced by oxygen, sulfur, NH, N—$CH_3$ or N-benzyl;
R(B), R(C), R(D) independently are defined as R(A);
x is zero or 1;
y is zero or 1;
R(F) is hydrogen, F, Cl, CN, OR(12), $(C_1-C_4)$-alkyl, $O_p(CH_2)_f C_g F_{2g+1}$, $(C_3-C_8)$-cycloalkyl or $(C_1-C_9)$-heteroaryl;
    p is zero or 1;
    f is zero, 1 or 2;
    g is 1, 2, 3 or 4;
    R(12) is $(C_1-C_4)$-alkyl, $(C_1-C_4)$-perfluoroalkyl, $(C_3-C_8)$-cycloalkyl, phenyl or benzyl, the phenyl nucleus being unsubstituted or substituted by 1–3 substituents selected from the group consisting of F, Cl, $CF_3$, methyl, methoxy and NR(13)R(14);
    R(13) and R(14) independently of one another are H, $CH_3$ or $CF_3$;
R(E) is defined as R(F);
R(1) is defined as T;
or
    R(1) is hydrogen, —$O_k C_m H_{2m+1}$, —$O_n C_q F_{2q+1}$, F, Cl, Br, I, CN, —(C=O)—N=C(NH_2)_2, —$So_r R(17)$, $SO_{r2}$—NR(31)R(32), —$O_u(CH_2)_v C_6 H_5$, —$O_{u2}$—$(C_1-C_9)$-heteroaryl or —$S_{u2}$—$(C_1-C_9)$-heteroaryl;
    k is zero or 1;
    m is zero, 1, 2, 3 or 4;
    n is zero or 1;
    q is 1, 2, 3 or 4;
    r is 2;
    r2 is zero, 1 or 2;
    R(31) and R(32) independently of one another are hydrogen, $(C_1-C_4)$-alkyl or $(C_1-C_4)$-perfluoroalkyl;
or
    R(31) and R(32) are together 4 or 5 methylene groups one of which can be replaced by oxygen, S, NH, N—$CH_3$ or N-benzyl;
    R(17) is $(C_1-C_4)$-alkyl;
    u is zero or 1;
    u2 is zero or 1;
    v is zero, 1 or 2;
    the phenyl nucleus being unsubstituted or substituted by 1–3 substituents selected from the group consisting of F, Cl, $CF_3$, methyl, methoxy, —$(CH_2)_w N(21)R(22)$, NR(18)R(19) and $(C_1-C_9)$-heteroaryl;
    R(18), R(19), R(21) and R(22) are H, $(C_1-C_4)$-alkyl or $(C_1-C_4)$-perfluoroalkyl;
    w is 1, 2, 3, 4;
    the heterocycle of the $(C_1-C_9)$-heteroaryl is unsubstituted or substituted by 1–3 substituents selected from the group consisting of F, Cl, $CF_3$, methyl and methoxy;
    R(2), R(3), R(4) and R(5) independently of one another are defined as R(1),
or
    R(1) and R(2) or R(2) and R(3) in each case together are —CH—CH=CH—CH—, which is unsubstituted or is substituted by 1–3 substituents selected from the group consisting of F, Cl, $CF_3$, methyl, methoxy, —$(CH_2)_{w2} NR(24)R(25)$ and NR(26)R(27);
    R(24), R(25), R(26) and R(27) are H, $CH_3$ or $CF_3$;
    W2 is 1, 2, 3 or 4;
wherein the radical T is only present twice in the molecule; and their pharmaceutically acceptable salts.

Particularly preferred compounds of the formula I are those in which: T is $$\left[\begin{array}{c}R(B)\\ \mid \\ R(A)\end{array}\right]_x \!\!\!\sim\!\!\! \left[\begin{array}{c}R(F)\\ \mid \\ \mid \\ R(E)\end{array} \begin{array}{c}R(D)\\ \mid \\ R(C)\end{array}\right]_y \!\!\!\sim\!\!\! \underset{O}{\overset{}{\mathrm{C}}}\!\!-\!\!\mathrm{N}\!\!=\!\!\mathrm{C}\!\!\begin{array}{c}NH_2\\ \\ NH_2\end{array}$$

x is zero;
y is zero;
R(F) is hydrogen, F, Cl, CN, OR(12), $(C_1-C_4)$-alkyl, —$O_p C_g F_{2g+1}$, $(C_3-C_8)$-cycloalkyl or $(C_1-C_9)$-heteroaryl;
    p is zero or 1;
    g is 1, 2, 3 or 4;
    R(12) is $(C_1-C_4)$-alkyl, $CF_3$, $(C_3-C_8)$-cycloalkyl, phenyl or benzyl, the phenyl nucleus in each case being unsubstituted or substituted by 1–3 substituents selected from the group consisting of F, Cl, $CF_3$, methyl, methoxy and NR(13)R(14);
    R(13) and R(14) are H, $CH_3$ or $CF_3$;
R(E) is defined as R(F);
R(1) is defined as T;
or
    R(1) is hydrogen, —$O_k C_m H_{2m+1}$, —$O_n C_q F_{2q+1}$, F, Cl, CN, —(C=O)—N=C(NH_2)_2, —$SO_2 CH_3$, $SO_2 NR(31)R(32)$, —$O_u(CH_2)_v C_6 H_5$, —$O_{u2}$—$(C_1-C_9)$-heteroaryl or —$S_{u2}$—$(C_1-C_9)$-heteroaryl;
    k is zero or 1;
    m is zero, 1, 2, 3 or 4;
    n is zero or 1;
    q is 1, 2, 3 or 4;
    R(31) and R(32) independently of one another are hydrogen or $(C_1-C_4)$-alkyl;
or
    R(31) and R(32) are together 4 or 5 methylene groups, one of which can be replaced by oxygen, S, NH, N—$CH_3$ or N-benzyl;
    u is zero or 1;
    u2 is zero or 1;
    v is zero or 1;
    the phenyl nucleus being unsubstituted or substituted by 1–3 substituents selected from the group consisting of F, Cl, $CF_3$, methyl, methoxy, —$(CH_2)_w N(21)R(22)$ and NR(18)R(19);
    R(18), R(19), R(21) and R(22) independently of one another are H, $(C_1-C_4)$-alkyl or $(C_1-C_4)$-perfluoroalkyl;
    w is 1, 2, 3 or 4;
    the heterocycle of the $(C_1-C_9)$-heteroaryl is unsubstituted or substituted by 1–3 substituents selected from the group consisting of F, Cl, $CF_3$, methyl and methoxy;
    R(2), R(3), R(4) and R(5) independently of one another are defined as R(1);

or

R(1) and R(2) or R(2) and R(3) in each case together are —CH—CH=CH—CH—, which is unsubstituted or is substituted by 1–3 substituents selected from the group consisting of F, Cl, $CF_3$, methyl, methoxy, —$(CH_2)_{w2}$NR(24)R(25) and NR(26)R(27);

R(24), R(25), R(26) and R(27) independently of one another are H, $(C_1-C_4)$-alkyl or $(C_1-C_4)$-perfluoroalkyl;

w2 is 1, 2, 3 or 4;

wherein the radical T is only present twice in the molecule; and their pharmaceutically acceptable salts.

The following compounds are very particularly preferred:
1,2-Bis[3-(E-2-methylpropenoic acid guanidide)]benzene dihydrochloride,
1,3-Bis[3-(E-2-methylpropenoic acid guanidide)]benzene dihydrochloride,
1,4-Bis[3-(E-2-methylpropenoic acid guanidide)]benzene dihydrochloride,
2,3-Bis[3-(E-2-methylpropenoic acid guanidide)]naphthalene dihydrochloride,
1,2-Bis[3-(Z-2-fluoropropenoic acid guanidide)]benzene dihydrochloride,
1-[3-(Z-2-fluoropropenoic acid guanidide)]-2-[3-(E-2-methylpropenoic acid guanidide)]benzene dihydrochloride,
1,3-Bis[3-(Z-2-fluoropropenoic acid guanidide)]benzene dihydrochloride,
3-(4-chloro-3-guanidinocarbonyl-5-phenyl)phenyl-2-methylpropenoic acid guanidide,
1,3-Bis[3-(E-2-methylpropenoic acid guanidide)]-2-methoxy-5-methyl-benzene hydrochloride,
1,2-Bis[3-(E-2-methylpropenoic acid guanidide)]4-methylbenzene dihydrochloride,
1,2-Bis[3-(E-2-methylpropenoic acid guanidide)]-4,5-dichlorobenzene dihydrochloride,
1,3-Bis[3-(E-propenoic acid guanidide)]benzene dihydrochloride,
1,2-Bis[3-(E-2-methylpropenoic acid guanidide)]-4-bromobenzene dihydrochloride,
1,2-Bis[3-(E-2-methylpropenoic acid guanidide)]-4-(4-methoxyphenoxy)-benzene dihydrochloride;
1,2-Bis[3-(E-2-methylpropenoic acid guanidide)]-4-(4-methylphenoxy)-benzene dihydrochloride,
1,3-Bis[3-(E-2-methylpropenoic acid guanidide)]-5-methoxybenzene hydrochloride,
1,3-Bis[3-(E-2-methylpropenoic acid guanidide)]-5-tert-butylbenzene hydrochloride,
1,4-Bis[3-(E-2-methylpropenoic acid guanidide)]-2,5-dichlorobenzene dihydrochloride,
1,2-Bis[3-(E-2-methylpropenoic acid guanidide)]-4-(phenoxy)benzene dihydrochloride,
1,2-Bis[3-(E-2-methylpropenoic acid guanidide)]-4-(methoxy)benzene dihydrochloride,
1,2-Bis[3-(E-2-methylpropenoic acid guanidide)]-4-(ethoxy)benzene dihydrochloride, and
1,2-Bis[3-(E-2-methylpropenoic acid guanidide)]-4-(3-pyridyloxy)benzene dihydrochloride.

If the compounds of the formula I contain one or more asymmetric centers, these can each have either the S or R configuration. The compounds can be present as optical isomers, as diastereomers, as racemates or as mixtures thereof.

The double bond geometry of the compounds of the formula I can be either E or Z. The compounds can be present in the mixture as double bond isomers.

The designated alkyl and perfluoroalkyl radicals can be either straight-chain or branched.

$(C_1-C_9)$-heteroaryl is understood in particular to mean radicals which are derived from phenyl or naphthyl, in which one or more CH groups are replaced by N and/or in which at least two adjacent CH groups are replaced by S, NH or O (with formation of a 5-membered aromatic ring). In addition, one or both atoms of the condensation site of bicyclic radicals, such as in indolizinyl, can also be nitrogen atoms.

Heteroaryl in particular includes furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl, and cinnolinyl.

The invention furthermore relates to a process for the preparation of a compound of formula I, which process comprises reacting a compound of the formula II

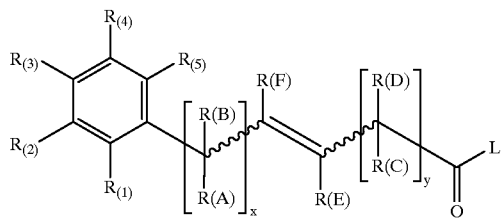

in which R(1), R(2), R(3), R(4), R(5), R(A), R(B), R(C), R(D), R(E), R(F), x and y have the meanings indicated above and L is an easily nucleophilically substitutable leaving group, with guanidine.

The activated acid derivatives of the formula II, in which L is an alkoxy group, preferably a methoxy group, a phenoxy group, phenylthio, methylthio or 2-pyridylthio group; or a nitrogen heterocycle, preferably 1-imidazolyl; are advantageously obtained in a manner known per se from the carboxylic acid chlorides (formula II, wherein L=Cl) on which they are based, which for their part can in turn be prepared in a manner known per se from the carboxylic acids (formula II, wherein L=OH) on which they are based, for example using thionyl chloride.

Beside the carboxylic acid chlorides of the formula II (wherein L=Cl), further activated acid derivatives of the formula II can also be prepared in a manner known per se directly from the alkenylcarboxylic acid derivatives (formula II, wherein L=OH) on which they are based, such as, for example, the methyl esters of the formula II where L=OCH_3 by treating with gaseous HCl in methanol, the imidazolides of the formula II by treating with carbonyldiimidazole [L=1-imidazolyl, Staab, Angew. Chem. Int. Ed. Engl. 1, 351–367 (1962)], the mixed anhydrides II with Cl—COOC_2H_5 or tosyl chloride in the presence of triethylamine in an inert solvent, and also the activation of alkenylcarboxylic acids with dicyclohexylcarbodiimide (DCC) or with O-[(cyano(ethoxycarbonyl)-methylene)amino]-1,1,3,3-tetramethyl-uronium tetrafluoroborate ("TOTU") [Proceedings of the 21st European Peptide Symposium, Peptides 1990, Editors E. Giralt and D. Andreu, Escom, Leiden, 1991]. A number of suitable methods for the preparation of activated carboxylic acid derivatives of the formula II are indicated with details of source literature in J. March, Advanced Organic Chemistry, Third Edition (John Wiley & Sons, 1985), p. 350.

The reaction of an activated carboxylic acid derivative of the formula II with guanidine is carried out in a manner known per se in a protic or aprotic polar, but inert, organic solvent. Methanol, isopropanol and THF from 20° C. up to the boiling temperature of these solvents have proven suitable in the reaction of the methyl alkenylcarboxylates (II, wherein L=OMe) with guanidine. Most reactions of compounds of formula II with salt-free guanidine were advantageously carried out in aprotic inert solvents such as THF, dimethoxyethane or dioxane. However, it is also possible to use water as a solvent in the reaction of a compound of formula II with guanidine if a base such as, for example, NaOH, is employed.

If L=Cl, the reaction is advantageously carried out with addition of an acid scavenger, e.g. in the form of excess guanidine, to bind the hydrohalic acid.

Some of the alkenylcarboxylic acid derivatives on which compounds of the formula II are based are known and described in the literature. The unknown compounds of the formula II can be prepared by methods known from the literature. The alkenylcarboxylic acids obtained are reacted according to one of the process variants described above to give compounds I according to the invention.

Some substituents can be introduced by methods known from the literature of palladium-mediated cross-coupling of aryl halides or aryl triflates with, for example, organostannanes, organoboronic acids, organoboranes or organocopper or -zinc compounds.

In general, alkenylguanidines of formula I are weak bases and are able to bind acid with formation of salts. Possible acid addition salts are salts of all pharmacologically tolerable acids, including, for example, halides, in particular hydrochlorides, lactates, sulfates, citrates, tartrates, acetates, phosphates, methanesulfonates, and p-toluenesulfonates.

The compounds of the formula I are substituted acylguanidines. The most prominent representatives of the acylguanidines are pyrazinecarboxylic acid and benzoic acid guanidides of the formulae V and VI.

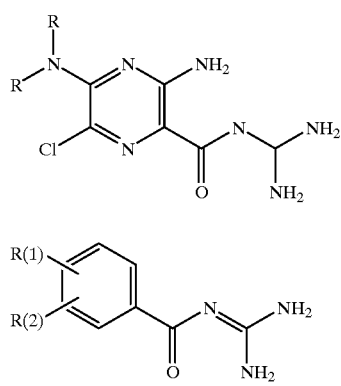

Amiloride: R, R'=H
Dimethylamiloride: R, R'=CH$_3$
Ethylisopropylamiloride: R=CH(CH$_3$)$_2$, R'=C$_2$H$_5$ Compounds of the formula V are generally described in the literature as amilorides. Amiloride itself (R, R'=H) is used in therapy as a potassium-sparing diuretic. Numerous other compounds of the amiloride type are described in the literature, such as, for example, dimethylamiloride or ethylisopropylamiloride.

Investigations exist which point to antiarrhythmic properties of amiloride [Circulation 79, 1257–63 (1989)]. An obstacle to wide use as an antiarrhythmic, however, is that this effect is only weakly pronounced and occurs accompanied by a hypotensive and saluretic action and these side effects are undesirable in the treatment of cardiac arrhythmias.

Indications of the antiarrhythmic properties of amiloride have also been obtained in experiments on isolated animal hearts [Eur. Heart J. 9 (suppl.1): 167 (1988) (book of abstracts)]. Thus it was found in rat hearts, for example, that it was possible to suppress artificially induced ventricular fibrillation completely by amiloride. The abovementioned amiloride derivative ethylisopropylamiloride was even more potent than amiloride in this model.

The compounds of the formula VI are selective inhibitors of the ubiquitous sodium/proton exchanger (subtype 1, NHE-1). Representatives known from the literature are HOE 694 and HOE 642, which are described as antiarrhythmic and, under ischemic conditions, as cardioprotective [(a) 25 Scholz W, Albus U, Linz W, Martorana P, Lang HJ, Schölkens BA. Effects of Na$^+$/H$^+$ exchange inhibitors in cardiac ischemia. J Mol Cell Cardiol 1992;24:731–739; (b) Scholz W, Albus U. Na$^+$/H$^+$ exchange and its inhibition in cardiac ischemia and reperfusion. Basic Res Cardiol 1993;88:443–455; (c) Scholz W, Albus U, Counillon L, Gögelein H, Lang HJ, Linz W, Weichert A, Schölkens BA. Protective effects of HOE 642, a selective sodium-hydrogen exchange subtype 1 inhibitor, on cardiac ischaemia and reperfusion. Cardiovasc Res 1995;29:260–268; (d) Bugge, E. and Ytrehus, K. Inhibition of sodium-hydrogen exchange reduces infarct size in the isolated rat heart—A protective additive to ischemic pre-conditioning. Cardiovasc. Res. 29:269–274, 1995.].

3-phenyl- and 3-thiophenylpropenoic acid guanidides of formula VII are furthermore known from the literature as NHE inhibitors [U.S. Pat. No. 2,734,904, WO 84/00875, German Offenlegungsschrift 44 21 536.3 (HOE 94/F 168)], but in these publications no bisguanidine compounds of the formula I are described or suggested.

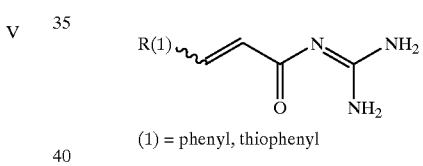

(1) = phenyl, thiophenyl

Surprisingly, the compounds of the formula I according to the invention inhibit the sodium/proton exchanger of subtype 3. The NHE inhibitors known to date are hardly active on this subtype.

The claimed compounds of the formula I have a hypotensive action and are thus suitable as pharmaceuticals for the treatment of primary and secondary hypertension. On account of their salidiuretic action, they are suitable as diuretics.

The compounds on their own or in combination with NHE inhibitors of other subtype specificity additionally have an antiischemic action. They protect organs which are acutely or chronically undersupplied with oxygen by reducing or preventing ischemically induced damage and are thus suitable as pharmaceuticals, for example in thrombosis, vasospasms, atherosclerosis or in surgical interventions (e.g., in kidney and liver organ transplantation, where the compounds can be used both for the protection of the organs in the donor before and during removal, for the protection of removed organs, for example during treatment with or storage thereof in physiological bath fluids, and in the transfer to the recipient's body) or acute or chronic kidney failure.

Corresponding to their protective action against ischemically induced damage, the compounds of the invention are also suitable as pharmaceuticals for the treatment of ischemias of the nervous system, in particular of the CNS, where they are suitable, for example, for the treatment of stroke or of cerebral edema. Moreover, the compounds of the formula I according to the invention are likewise suitable for the treatment of forms of shock, such as, for example, of allergic, cardiogenic, hypovolemic and of bacterial shock.

The compounds of the invention furthermore induce an improvement in the respiratory drive and are therefore used for the treatment of respiratory conditions in the following clinical conditions and illnesses: Impaired central respiratory drive (e.g., central sleep apneas, sudden infant death, postoperative hypoxia); muscle-related respiratory disorders; respiratory disorders after long-term respiration; respiratory disorders during adaptation in a high mountain region; obstructive and mixed forms of sleep apneas; acute and chronic lung diseases with hypoxia, and hypercapnia.

A combination of an NHE inhibitor with a carboanhydrase inhibitor (e.g. acetazolamide), the latter producing a metabolic acidosis and thereby even increasing the respiratory activity, proves to be a favorable combination with increased action and decreased use of active compound.

The compounds of the formula I according to the invention are moreover distinguished by strong inhibitory action on the proliferation of cells, for example fibroblast cell proliferation and the proliferation of vascular smooth muscle cells. The compounds of the formula I are therefore suitable as valuable therapeutics for illnesses in which cell proliferation is a primary or secondary cause, and can therefore be used as antiatherosclerotics, agents against diabetic late complications, carcinomatous disorders, fibrotic disorders such as pulmonary fibrosis, hepatic fibrosis or renal fibrosis, endothelial dysfunction, organ hypertrophies and hyperplasias, in particular in prostate hyperplasia or prostate hypertrophy. The compounds additionally bring about a lowering of the cholesterol level and are thereby suitable as pharmaceuticals for the prevention and treatment of atherosclerosis.

The compounds according to the invention are also effective inhibitors of the cellular sodium-proton antiporter ($Na^+/H^+$ exchanger), subtype 1 and 3, which is relevant in numerous disorders (essential hypertension, atherosclerosis, diabetes, etc.) even in those cells which are easily accessible to measurements, such as, for example, in erythrocytes, platelets or leucocytes. The compounds according to the invention are therefore suitable as outstanding and simple scientific tools, for example in their use as diagnostics for the determination and differentiation of certain forms of hypertension, but also of atherosclerosis, diabetes, proliferative disorders, etc. Moreover, the compounds of the formula I are suitable for preventive therapy for preventing the genesis of high blood pressure, for example of essential hypertension.

It has additionally been found that compounds of the formula I have a favorable influence on serum lipoproteins. It is generally recognized that for the formation of arteriosclerotic vascular changes, in particular of coronary heart disease, excessively high blood lipid values, so-called hyperlipoproteinemias, are a significant risk factor. The lowering of raised serum lipoproteins is therefore of extreme importance for the prophylaxis and the regression of atherosclerotic changes. Beside the reduction of the serum total cholesterol, the lowering of the proportion of specific atherogenic lipid fractions of this total cholesterol, in particular of the low density lipoproteins (LDL) and of the very low density lipoproteins (VLDL) has particular importance, as these lipid fractions are an atherogenic risk factor. In contrast, the high density lipoproteins are ascribed a protective function against coronary heart disease. Accordingly, hypolipidemics should be able to lower not only the total cholesterol, but in particular the VLDL and LDL serum cholesterol fractions.

It has now been found that compounds of the formula I have valuable therapeutically utilizable properties with respect to influencing the serum lipid levels. Thus they significantly lower the increased serum concentrations of LDL and VLDL, as are to be observed, for example, due to increased dietetic intake of a cholesterol- and lipid-rich diet or in pathological metabolic changes, for example genetically related hyperlipidemias. They can therefore be used for the prophylaxis and for the regression of atherosclerotic changes, in that they exclude a causal risk factor. These include not only the primary hyperlipidemias, but also certain secondary hyperlipidemias, such as occur, for example, in diabetes. Moreover, the compounds of the formula I lead to a distinct reduction in the infarcts induced by metabolic anomalies and in particular to a significant decrease in the induced infarct size and its degree of severity. Furthermore, compounds of the formula I lead to effective protection against endothelial damage induced by metabolic anomalies. With this protection of the vessels against the endothelial dysfunction syndrome, compounds of the formula I are valuable pharmaceuticals for the prevention and for the treatment of coronary vasospasms, atherogenesis and atherosclerosis, left-ventricular hypertrophy and dilated cardiomyopathy, and thrombotic disorders.

The compounds mentioned in this application are therefore used advantageously for the production of a medicament for the treatment of hypercholesterolemia; for the production of a medicament for the prevention of atherogenesis; for the production of a medicament for the prevention and treatment of atherosclerosis; for the production of a medicament for the prevention and treatment of diseases which are caused by increased cholesterol levels; for the production of a medicament for the prevention and treatment of diseases which are caused by endothelial dysfunction; for the production of a medicament for the prevention and treatment of atherosclerosis-induced hypertension; for the production of a medicament for the prevention and treatment of atherosclerosis-induced thrombosis; for the production of a medicament for the prevention and treatment of hypercholesterolemia- and endothelial dysfunction-induced ischemic damage and postischemic reperfusion damage, for the production of a medicament for the prevention and treatment of hypercholesterolemia- and endothelial dysfunction-induced cardiac hypertrophies and cardiomyopathies; for the production of a medicament for the prevention and treatment of hypercholesterolemia- and endothelial dysfunction-induced coronary vasospasms and myocardial infarcts; and for the production of a medicament for the treatment of the illnesses mentioned in combinations with hypotensive substances, preferably with angiotensin-converting enzyme (ACE) inhibitors and angiotensin receptor antagonists, a combination of an NHE inhibitor of the formula I with a blood lipid level-lowering active compound, preferably with a HMG-CoA-reductase inhibitor (e.g. lovastatin or pravastatin), where the latter produces a hypollpidemic action and thereby increases the hypolipidemic properties of the NHE inhibitor of the formula I, and proves to be a favorable combination with increased action and decreased use of active compound.

The administration of sodium/proton exchange inhibitors of the formula I as novel pharmaceuticals for lowering increased blood lipid levels is claimed, as is the combination of sodium/proton exchange inhibitors with hypotensive and/or hypolipidemic pharmaceuticals:

Pharmaceuticals which contain a compound of formula I can in this case be administered orally, parenterally, intravenously, rectally or by inhalation; the preferred administration being dependent on the particular clinical picture of the disorder. The compounds of formula I can in this case be used on their own or together with pharmaceutical auxiliaries, to be specific both in veterinary and in human medicine.

The person skilled in the art is familiar on the basis of his expert knowledge with auxiliaries which are suitable/acceptable for the desired pharmaceutical formulation. Beside solvents, gel-forming agents, suppository bases, tablet auxiliaries and other active compound excipients, it is possible to use, for example, antioxidants, dispersants, emulsifiers, antifoams, flavor corrigents, preservatives, solubilizers and colorants.

For an oral administration form, the active compounds are mixed with the additives acceptable for this, such as excipients, stabilizers or inert diluents, and are brought by means of the customary methods into the acceptable administration forms, such as tablets, coated tablets, hard gelatin capsules, or aqueous, alcoholic or oily solutions. Inert excipients which can be used are, for example, gum arabic, magnesia, magnesium carbonate, potassium phosphate, lactose, glucose and starch, in particular corn starch. In this case preparation can take place either as dry or as moist granules. Acceptable oily excipients or solvents are, for example, vegetable or animal oils, such as sunflower oil and cod liver oil.

For subcutaneous or intravenous administration, the active compounds are brought into solution, suspension or emulsion, if desired using the substances customary for this, such as solubilizers, emulsifiers or other auxiliaries. Possible solvents are, for example: water, physiological saline solution or alcohols, e.g., ethanol, propanol, glycerol, in addition also sugar solutions such as glucose or mannitol solutions, or alternatively a mixture of the various solvents mentioned.

Suitable pharmaceutical formulations for administration in the form of aerosols or sprays are, for example, solutions, suspensions or emulsions of the active compound(s) of the formula I in a pharmaceutically acceptable solvent, such as, in particular, ethanol or water, or a mixture of such solvents.

If required, the formulation can also contain other pharmaceutical auxiliaries such as surfactants, emulsifiers and stabilizers, as well as a propellant. Such a preparation contains the active compound(s) customarily in a concentration of from approximately 0.1 to 10, in particular from approximately 0.3 to 3%, by weight.

The dose of the active compound(s) of the formula I to be administered and the frequency of administration depend on the potency and duration of action of the compounds used; additionally on the nature and severity of the illness to be treated and on the sex, age, weight and individual responsiveness of the mammal to be treated. On average, the daily dose of a compound of the formula I in the case of a patient approximately 75 kg in weight is at least 0.001 mg/kg, preferably 0.01 mg/kg, to at most 10 mg/kg, preferably 1 mg/kg, of body weight. In acute episodes of the illnesses, even higher and especially more frequent doses may also be necessary, e.g. up to 4 individual doses per day. In particular, on i.v. administration, for example in the case of an infarct patient in the intensive care unit, up to 200 mg per day may be necessary.

| MeOH | Methanol |
| DMF | N,N-dimethylformamide |
| EI | Electron impact |
| DCI | Desorption-chemical ionisation |
| RT | Room temperature |
| EE | Ethyl acetate (EA) |
| mp | Melting point |
| HEP | n-Heptane |
| DME | Dimethoxyethane |
| ES | Electron spray |
| FAB | Fast atom bombardment |
| $CH_2Cl_2$ | Dichlormethane |
| THF | Tetrahydrofuran |
| eq. | Equivalent |

Experimental section

General procedure for the preparation of alkenylcarboxylic acid guanidides (I)

Variant 1 A: from alkenylcarboxylic acids (II, wherein L=OH)

1.0 eq. of the carboxylic acid derivative of the formula 11 was dissolved or suspended in anhydrous THF (5 ml/mmol) and then treated with 1.1 eq. of carbonyldiimidazole. After stirring for 2 hours at RT, 5.0 eq. of guanidine were introduced into the reaction solution. After stirring overnight, the THF was distilled off under reduced pressure (rotary evaporator), the residue was treated with water, the mixture was adjusted to pH 6 to 7, using 2N HCl and the corresponding guanidide (formula I) was filtered off. The carboxylic acid guanidides thus obtained could be converted into the corresponding salts by treating with aqueous, methanolic or ethereal hydrochloric acid or other pharmacologically tolerable acids.

Variant 1 B: from alkyl alkenylcarboxylates (II, wherein L=O-alkyl)

1.0 eq. of the alkyl carboxylate of the formula II and 5.0 eq. of guanidine (free base) were dissolved in isopropanol or suspended in THF and refluxed (typical reaction time 2 to 5 h) until conversion was complete (thin-layer checking). The solvent was distilled off under reduced pressure (rotary evaporator), the residue was taken up in EA and the solution was washed 3× with $NaHCO_3$ solution. It was dried over $Na_2SO_4$, the solvent was distilled off in vacuo and the residue was chromatographed on silica gel using a suitable eluent, e.g. EA/MeOH 5:1. (For salt formation compare Variant A)

Example 1: 1,2-Bis[3-(E-2-methylpropenoic acid guanidide)]benzene dihydrochloride

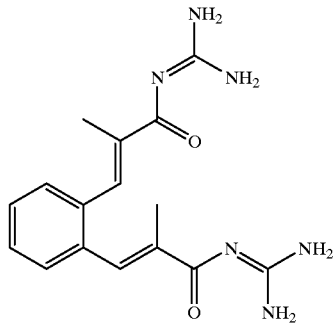

1a) 1 eq. of triethyl 2-phosphonopropionate was deprotonated at 0° C. using 1 eq. of n-butyllithium in hexane and then treated at RT with 0.5 eq. of 1,2-phthalaldehyde. After reaction of the dialdehyde was complete, the mixture was worked up using water and extracted three times by shaking with toluene. After drying the combined organic phases over magnesium sulfate, the solvent was removed in vacuo and the residual crude product was separated chromatographically on silica gel using EA/HEP mixtures as eluent.

Isolated: 1,2-Di[3-(E-2-methylpropenoate)]benzene.

Colorless oil: MS (DCl): 303 ((M+1)+)

1b) The ester from 1a) was hydrolyzed according to a standard method (sodium hydroxide in methanol). Isolated: 1,2-Di[3-(E-2-methylpropenoic acid)]benzene.

Colorless solid;

mp:>187° C. MS (DCl): 246 (M$^+$)

1c) The dicarboxylic acid from 1b) was converted into the diguanidide dihydrochloride according to Variant 1 A.

Colorless solid;

mp:>200° C.; MS (DCl): 329 ((M+1)$^+$)

Example 2: 1,3-Bis[3-(E-2-methylpropenoic acid guanidide)]benzene dihydrochloride

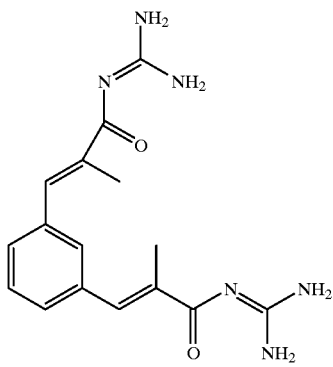

2a) 1 eq. of triethyl 2-phosphonopropionate was deprotonated at 0° C. using 1 eq. of n-butyllithium in hexane and then treated at RT with 0.5 eq. of 1,3-isophthalaldehyde. After reaction of the dialdehyde was complete, the mixture was worked up with water and extracted three times by shaking with toluene. After drying the combined organic phases over magnesium sulfate, the solvent was removed in vacuo and the residual crude product was separated chromatographically on silica gel using EA/NHEP mixtures as eluent.

Isolated: 1,3-Di[3-(ethyl E-2-methylpropenoate)]benzene.

Colorless oil; MS (DCl): 303 ((M+1)$^+$)

2b) The ester from 2a) was hydrolyzed according to a standard method (sodium hydroxide in methanol). Isolated: 1,3-Di[3-(E-2-methylpropenoic acid)]benzene.

Colorless solid;

mp>190° C.; MS (DC): 247 ((M+1)$^+$)

2c) The dicarboxylic acid from 2b) was converted into the diguanidide dihydrochloride according to Variant 1 A.

Colorless solid;

Mp: 175° C.; MS (DCl): 329 ((M+1)$^+$)

Example 3: 1,4-Bis[3-(E-2-methylpropenoic acid guanidide)]benzene dihydrochloride

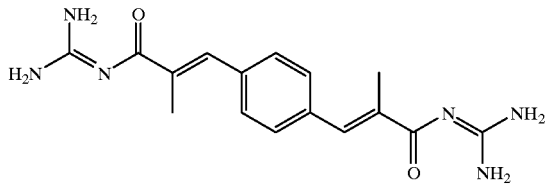

3a) 1 eq. of triethyl 2-phosphonopropionate was deprotonated at 0° C. using 1 eq. of n-butyllithium in hexane and then treated at RT with 0.5 eq. of 1,4-terephthalaldehyde. After reaction of the dialdehyde was complete, the mixture was worked up with water and extracted three times by shaking with toluene. After drying the combined organic phases over magnesium sulfate, the solvent was removed in vacuo and the residual crude product was separated chromatographically on silica gel using EA/HEP mixtures as eluent. Isolated: 1,4-Di[3-(ethyl E-2-methylpropenoate)]benzene.

Colorless solid;

mp: 41° C.; MS (DCl): 303 ((M+1)$^+$)

3b) The ester from 3a) was hydrolyzed according to a standard method (sodium hydroxide in methanol). Isolated: 1,4-Di[3-(E-2-methylpropenoic acid)]benzene.

Colorless solid;

mp:>190° C.; MS (DCl): 247 ((M+1)$^+$)

3c) The dicarboxylic acid from 3b) was converted into the diguanidide dihydrochloride according to Variant 1 A.

Yellow solid;

mp: 255° C.; MS (DCl): 329 ((M+1)$^+$)

Example 4: 2,3-Bis[3-(E-2-methylpropenoic acid guanidide)]naphthalene dihydrochloride

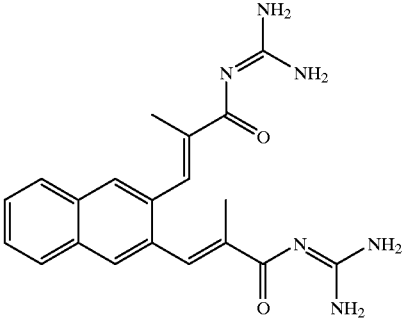

4a) 1 eq. of triethyl 2-phosphonopropionate was deprotonated at 0° C. using 1 eq. of n-butyllithium in hexane and then treated at RT with 0.5 eq. of 2,3-naphthalenedicarboxaldehyde. After reaction of the dialdehyde was complete, the mixture was worked up with water and extracted three times by shaking with toluene. After drying the combined organic phases over magnesium sulfate, the solvent was removed in vacuo and the residual crude product was separated chromatographically on silica gel using EA/HEP mixtures as eluent. Isolated: 2,3-Di[3-(ethyl E-2-methylpropenoate)]napthalene.

Colorless oil; MS (DCl): 353 ((M+1)$^+$)

4b) The ester from 4a) was hydrolyzed according to a standard method (sodium hydroxide in methanol). Isolated: 2,3-Di[3-(E-2-methylpropenoic acid)]napthalene.

Colorless solid;

mp: >210° C.; MS (DCl): 295 (M—H)⁻

4c) The dicarboxylic acid from 4b) was converted into the diguanidide dihydrochloride according to Variant 1 A.

Colorless solid;

mp: >200° C.; MS (DCl): 379 ((M+1)$^+$)

Example 5: 1,2-Bis[3-(Z-2-fluoropropenoic acid guanidide)]benzene dihydrochloride

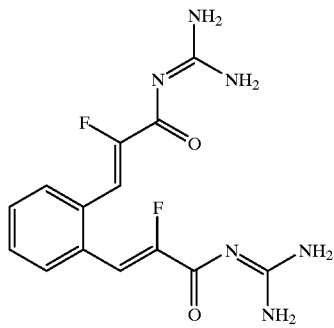

5a) Following a process known from the literature (Cousseau et al., Tetrahedron Letters 34, 1993, 6903), starting, from 1,2-phthalaldehyde 1,2-Di[3-(ethyl Z-2-fluoropropenoate)]benzene was prepared and purified and isolated on silica gel using EA/HEP mixtures as eluent.

Colorless solid;

mp: amorphous; MS (DCl): 311 ((M+1)$^+$)

5b) The diester from 5a) was reacted to give the diguanidide according to Variant 1 B and converted into the dihydrochloride.

Mp.: >235° C.; MS (DCl): 337 ((M+1)$^+$)

Example 6: 1-[3-(Z-2-Fluoropropenoic acid guanidide)]-2-[3-(E-2-methylpropenoic acid guanidide)]benzene dihydrochloride

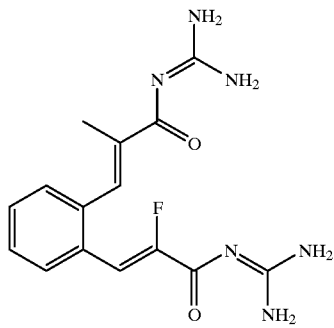

6a) The monoaldehyde monoester 6a) also isolated in the preparation of 7a) was converted into the diester 6b) following 4a).

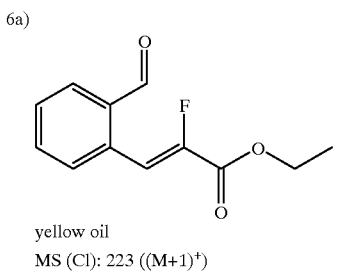

yellow oil
MS (Cl): 223 ((M+1)$^+$)

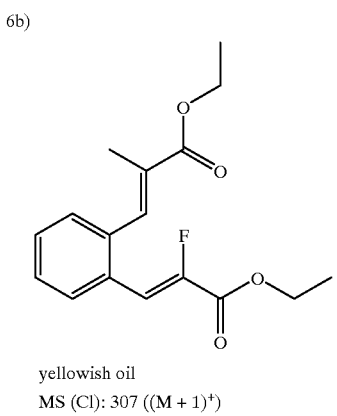

yellowish oil
MS (Cl): 307 ((M + 1)$^+$)

6c) The diester from 6b) was reacted to give the diguanidide according to Variant 1 B and converted into the dihydrochloride.

Mp: >200° C.; MS (ES): 333 ((M+1)$^+$)

Example 7: 1,3-Bis[3-(Z-2-fluoropropenoic acid guanidide)]benzene dihydrochloride

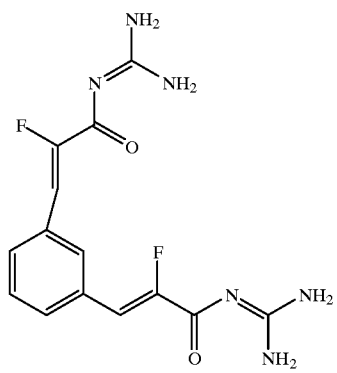

7a) Following a process known from the literature (Cousseau et al., Tetrahedron Letters 34, 1993, 6903), starting from 1,3-isophthalaldehyde 1,3-Di[3-(ethyl Z-2-fluoropropenoic acid)]benzene was prepared and purified and isolated on silica gel using EA/HEP mixtures as eluent.

Colorless solid;

mp: amorphous; MS (Cl): 311 ((M+1)$^+$)

7b) The diester from 7a) was reacted to give the diguanidide according to Variant 1 B and converted into the dihydrochloride.

Orange/yellow-colored solid;

Mp: >180° C.; MS (ES): 337 ((M+1)$^+$)

Example 8: 3-(4-Chloro-3-guanidinocarbonyl-5-phenyl)phenyl-2-methylpropenoic acid guanidide

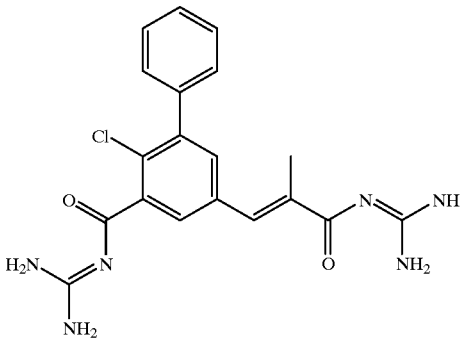

8a) 3-Bromo-2-chloro-5-methylbenzoic acid 25 g of 2-amino-3-bromo-5-methylbenzoic acid were dissolved in 500 ml of 6N aqueous HCl solution, treated at 0° C. with 8.25 g of NaNO$_2$ and diazotized at this temperature for 30 minutes. This diazonium salt solution was then added dropwise to a warm solution of 22 g of CuCl in 200 ml of a saturated aqueous HCl solution at 40° C. and the mixture was stirred at this temperature for 20 minutes. The product was filtered off with suction, washed with 500 ml of water and dried at 40° C. in a fine vacuum.

23.3 g of white crystals were obtained;

mp 170–172° C.; R$_f$(EA/MeOH 5:1)=0.51; MS (DCl): 249 (M+H)$^+$ 8 b) 3-Bromo-2-chloro-5-dibromomethylbenzoic acid 10 g of 3-bromo-2-chloro-5-methylbenzoic acid were dissolved in 150 ml of chlorobenzene and the solution was heated to reflux. Firstly 7.2 g of N-bromosuccinimide and 0.5 g of benzoyl peroxide were added at this temperature and the mixture was refluxed for 30 minutes. 7.2 g of N-bromosuccinimide and 0.5 g of benzoyl peroxide were then added a second time and the mixture was refluxed for a further 3 hours. After cooling, 200 ml of EA were added, the mixture was washed with 50 ml of saturated aqueous Na$_2$SO$_3$ solution/300 ml of saturated aqueous KH$_2$PO$_4$ solution and the aqueous phase was extracted 2 times using 200 ml of EA each time. The organic phase was dried over Na$_2$SO$_4$ and the solvent was removed in vacuo. 14.1 g of a yellow oil were obtained.

R$_f$ (DIP/2% HOAc)=0.32

8c) 3-Bromo-2-chloro-5-formylbenzoic acid 11.7 g of AgNO$_3$ were dissolved in 150 ml of water and 150 ml of MeOH and a solution of 14 g of 3-bromo-2-chloro-5-dibromomethylbenzoic acid in 100 ml of MeOH was added dropwise. The mixture was stirred at RT for 30 minutes, 100 ml of a saturated aqueous NaCl solution were added, the silver salts were filtered off with suction and the solvents were removed in vacuo. The residue was taken up using 200 ml of a 5% aqueous KHSO$_4$ solution and extracted 3 times using 200 ml of EA each time. The organic phase was dried over Na$_2$SO$_4$ and the solvent was removed in vacuo. Chromatography on silica gel using DIP/2% HOAc yielded 3.6 g of colorless crystals;

mp: 148° C.; R$_f$(DIP/2% HOAc)=0.12; MS (DCl): 263 (M+H)$^+$

8d) Ethyl 3-bromo-2-chloro-5-formylbenzoate 3.6 g of 3-bromo-2-chloro-5-formylbenzoic acid were dissolved in 100 ml of 20 EtOH, 2.9 ml of SOCl$_2$ were added dropwise and the mixture was refluxed for 5 hours. The volatile constituents were then removed in vacuo and the residue was chromatographed on silica gel using EA/HEP 1:8. 2.7 g of a colorless oil were obtained.

R$_f$(EA/HEP 1:8)=0.24; MS (DCl): 291 (M+H)$^+$

8e) Ethyl 3-(3-bromo-4-chloro-5-ethoxycarbonyl)phenyl-2-methylpropenoate 2.7 g of ethyl 3-bromo-2-chloro-5-formylbenzoate were subjected to a Wittig-Horner reaction analogously to Example 4a), and 3.4 g of a colorless oil were obtained.

R$_f$(EA/HEP 1:8)=0.27; MS (DCl): 374 (M+H)$^+$

8f) Ethyl 3-(4-chloro-3-ethoxycarbonyl-5-phenyl)phenyl-2-methylpropenoate 3.3 g of ethyl 3-(3-bromo-4-chloro-5-ethoxycarbonyl)phenyl-2-methylpropenoate, 1.23 g of phenylboronic acid, 2.14 g of Na$_2$CO$_3$, 576 mg of triphenylphosphine and 227 mg of Pd(OAc)$_2$ were dissolved in 150 ml of toluene and 40 ml of water and the solution was refluxed for 7 hours. It was then cooled to RT, treated with 200 ml of EA and washed 2 times with 100 ml each time of a saturated aqueous Na$_2$CO$_3$ solution and also with 100 ml of a saturated aqueous NaCl solution, dried over Na$_2$SO$_4$ and the solvent was removed in vacuo. Chromatography on silica gel using EA/HEP 1:8 yielded 800 mg of a colorless oil.

Rf (EA/HEP 1:8)=0.25; MS (DCl): 372 (M+H)$^+$ 8g) 3-(4-Chloro-3-guanidinocarbonyl-5-phenyl)phenyl-2-methylpropenoic acid guanidide 1.8 g of potassium t-butoxide were dissolved in 100 ml of DMF, 1.82 g of guanidine hydrochloride were added and the mixture was stirred at RT for 1 hour. 700 mg of ethyl 3-(4-chloro-3-ethoxycarbonyl-5-phenyl)phenyl-2-methylpropenoate were added and the mixture was stirred at 100° C. for 5 hours. The reaction mixture was poured onto 200 ml of water and extracted 3 times using 200 ml of EA each time. The organic phase was dried over Na$_2$SO$_4$ and the solvent was removed in vacuo. Chromatography on silica gel using acetone/water 10:1 yielded 170 mg of an amorphous foam.

Rf (acetone/water 10:1)=0.23; MS (FAB): 399 (M+H)$^+$

Example 9: 1,3-Bis[3-(E-2-methylpropenoic acid guanidide)]-2-methoxy-5-methylbenzene hydrochloride

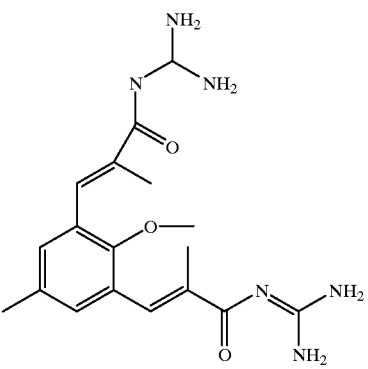

9a) 1 eq. of triethyl 2-phosphonopropionate was deprotonated at 0° C. using 1 eq. of n-butyllithium in hexane and then treated at RT with 0.5 eq. of 2-methoxy-5-methyl-1,3-isophthalaldehyde. After reaction of the dialdehyde was complete, the mixture was worked up using water and extracted three times by shaking with toluene. After drying the combined organic phases over magnesium sulfate, the solvent was removed in vacuo and the residual crude product was separated chromatographically on silica gel using EA/HEP mixtures as eluent. Isolated: 1 3-Di[3-(ethyl E-2-methylpropenoate)]-2-methoxy-5-methylbenzene.

Colorless oil; MS (Cl): 347 ((M+1)$^+$)

9b) The diester from 9a) was hydrolyzed according to a standard method (sodium hydroxide in methanol). Isolated: 1,3-Di[3-(E-2-methylpropenoic acid)]-2-methoxy-5-methylbenzene.

Colorless solid;

Mp: 196° C.; MS (DCl): 290 (M)$^+$

9c) The dicarboxylic acid from b) was converted into the diguanidide according to Variant 1 A and isolated as the hydrochloride.

Colorless solid;

Mp: 279° C.; MS (NBA): 373 ((M+1)$^+$)

Example 10: 1,2-Bis[3-(E-2-methylpropenoic acid guanidide)]-4-methyl-benzene dihydrochloride

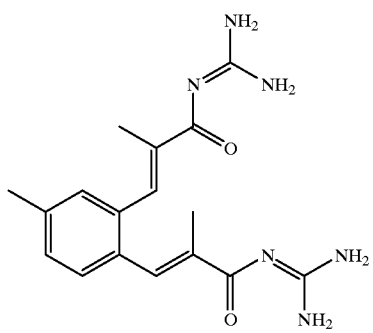

10a, b) 4-Methylphthalic acid diester was converted into the dialcohol 10a) according to a standard method (e.g. reduction with lithium aluminum hydride). The alcohol was then oxidized to the dialdehyde 10b) under standard conditions (e.g. Swern Oxidation).

Dialcohol 10a): Colorless oil; MS (DC1): 153 ((M+1)$^+$) and 135 (M+1-H$_2$O).

Dialdehyde 10b): Dark oil; MS (Cl): 149 ((M+1)$^+$)

10c) 1 eq. of triethyl 2-phosphonopropionate was deprotonated at 0° C. using 1 eq. of n-butyllithium in hexane and then treated at RT with 0.5 eq. of 4-methyl-1,2-phthalaldehyde 10b). After reaction of the dialdehyde was complete, the mixture was worked up using water and extracted three times by shaking with toluene. After drying the combined organic phases over magnesium sulfate, the solvent was removed in vacuo and the residual crude product was separated chromatographically on silica gel using EA/HEP mixtures as eluent. Isolated: 4-Methyl-1,2-Di[3-(ethyl E-2-methylpropenoate)]benzene.

Colorless oil; MS (Cl): 317 ((M+1)$^+$)

10d) The ester from 10c) was hydrolyzed according to a standard method (sodium hydroxide in methanol). Isolated: 4-Methyl-1,2-Di[3-(E-2-methyl-propenoic acid)]benzene.

Colorless solid;

Mp: 194–198° C.; MS (Cl): 260 (M)$^+$

10e) The dicarboxylic acid from 10d) was converted into the dig uanidide dihydrochloride according to Variant 1 A.

Colorless solid;

Mp: 190° C.; MS (ES): 342 ((M+1)$^+$)

Example 11: 1,2-Bis[3-(E-2-methylpropenoic acid)]-4,5-dichlorobenzene dihydrochloride

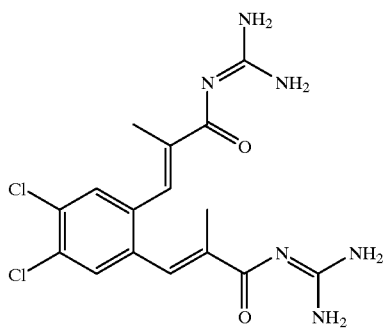

11a,b) Diethyl 4,5-dichlorophthalate was converted into the dialcohol 11a) according to a standard method (e.g. reduction with lithium aluminum hydride). The alcohol was then oxidized to the dialdehyde 11 under standard conditions (e.g. Swern oxidation).

Dialcohol 11a): Colorless solid, Mp 147° C.; MS (Cl): 207 ((M+1)$^+$)

Dialdehyde 11b): Amorphous solid, MS (Cl): 203 ((M+1)$^+$)

11c) 1 eq. of triethyl 2-phosphonopropionate was deprotonated at 0° C. using 1 eq. of n-butyllithium in hexane and then treated at RT with 0.5 eq. of 4,5-dichloro-1,2-phthalaldehyde 11b). After complete reaction of the dialdehyde, the mixture was worked up using water and extracted three times by shaking with toluene. After drying the combined organic phases over magnesium sulfate, the solvent was removed in vacuo and the residual crude product was separated chromatographically on silica gel using EA/HEP mixtures as eluent. Isolated: 4,5-Dichloro-1,2-Di[3-(ethyl E-2-methylpropenoate)]benzene.

Colorless solid;

Mp: >230° C.; MS (Cl): 371 ((M+1)$^+$)

11d) The diester from 11c) was converted into the diguanidide dihydrochloride according to Variant 1 B.

Colorless solid;

Mp: >220° C.; MS (ES): 397 ((M+1)$^+$)

Example 12: 1,3-Bis[3-(E-propenoic acid guanidide)]benzene dihydrochloride

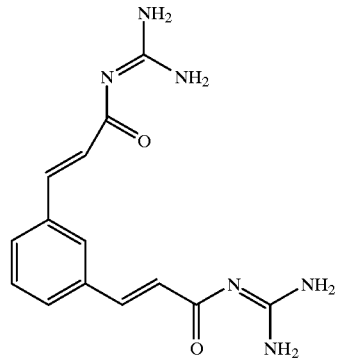

12a) 1 eq. of triethyl phosphonoacetate was deprotonated at 0° C. using 1 eq. of n-butyllithium in hexane and then treated at RT with 0.5 eq. of 1,3-isophthalaldehyde. After complete reaction of the dialdehyde, the mixture was worked up using water and extracted three times by snaking with toluene. After drying the combined organic phases over magnesium sulfate, the solvent was removed in vacuo and the residual crude product was separated chromatographically on silica gel using EA/HEP mixtures as eluent. Isolated: 1,3-Di[3-(ethyl E-propenoate)]benzene.

Colorless oil; MS (Cl): 275 ((M+1)$^+$)

12b) The diesterfrom 12a) was hydrolyzed according to a standard method (sodium hydroxide in methanol). Isolated: 1,3-Di[3-(E-propenoic acid)]benzene.

Colorless solid;

Mp: >200° C.; MS (DCl): 217 (M−1)$^+$

12c) The dicarboxylic acid from 12b) was converted into the diguanidide dihydrochloride according to Variant 1 A.

Colorless solid;

Mp: 296° C.; MS (ES): 301 ((M+1)$^+$)

Example 13: 1,2-Bis[3-(E-2-methylpropenoic acid guanidide)]-4-bromobenzene dihydrochloride

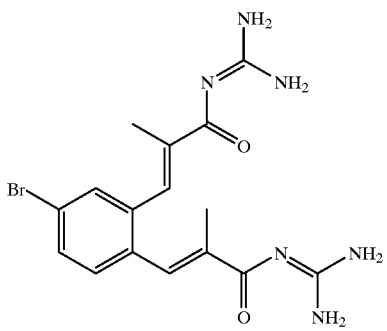

13a, b) Dimethyl 4-bromophthalate was converted into the dialcohol 13a) according to a standard method (e.g. reduction with lithium aluminum hydride). The alcohol was then oxidized to the dialdehyde 13b) under standard conditions (e.g. Swern oxidation).

Dialcohol 13a): Colorless oil; MS (DCl): 217 ((M+1)$^+$) and 199 (M+1−H$_2$O).

Dialdehyde 13b): Amorphous solid, MS (Cl): 213 ((M+1)$^+$)

13c) 1 eq. of triethyl 2-phosphonopropionate was deprotonated at 0° C. using 1 eq. of n-butyllithium in hexane and then treated at RT with 0.5 eq. of 4-bromo-1,2-phthalaldehyde. After complete reaction of the dialdehyde, the mixture was worked up using water and extracted three times by shaking with toluene. After drying the combined organic phases over magnesium sulfate, the solvent was removed in vacuo and the residual crude product was separated chromatographically on silica gel using EA/HEP mixtures as eluent. Isolated: 4-Bromo-1,2-Di[3-(ethyl E-2-methylpropenoate)]benzene.

Colorless oil; MS (Cl): 381 ((M+1)$^+$)

13d) The ester from 13c) was hydrolyzed according to a standard method (sodium hydroxide in methanol). Isolated: 4-Bromo-1,2-Di[3-(E-2-methyl-propenoic acid)]benzene.

Colorless amorphous solid; MS (ES): 325 ((M+1)$^+$)

13e) The dicarboxylic acid from 13e) was converted into the dig uanidide dihydrochloride according to Variant 1 A.

Colorless solid;

Mp: 240° C.; MS (FAB): 407 ((M+1)$^+$)

Example 14: 1,2-Bis[3-(E-2-methylpropenoic acid guanidide)]-4-(4-methoxyphenoxy)benzene dihydrochloride

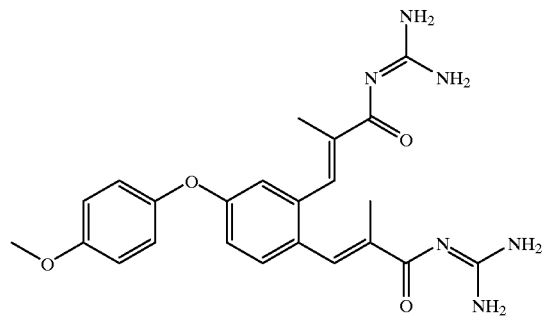

14a) Dimethyl 4-nitrophthalate was reacted in DMF with sodium 4-methoxyphenoxide to give dimethyl 4-(4-methoxyphenoxy)phthalate in analogy to a process known from the literature (J. Org. Chem. Vol. 42, No. 21, 1977, 3419–3425). After standard working up and chromatography using hexane/EA, the diester was isolated as a brownish oil.

MS (Cl): 316 (M+): 317 ((M+1)$^+$).

14b,c) The diester 14a) was converted into the dialcohol 14b) according to a standard method (e.g. reduction with lithium aluminum hydride). The alcohol was then oxidized to the dialdehyde 14c) under standard conditions (e.g. Swern oxidation).

Dialcohol 14b): Brownish oil; MS (Cl): 260 (M)+.

Dialdehyde 14c): Brownish oil; MS (Cl): 257 ((M+1)$^+$).

14d) 1 eq. of triethyl 2-phosphonopropionate was deprotonated at 0° C. using 1 eq. of n-butyllithium in hexane and then treated at RT with 0.5 eq. of 1,2-phthalaldehyde 14c). After complete reaction of the dialdehyde, the mixture was worked up using water and extracted three times by shaking with toluene. After drying the combined organic phases over magnesium sulfate, the solvent was removed in vacuo and the residual crude product was separated chromatographically on silica gel using EA/HEP mixtures as eluent.

Isolated: 1,2-Di[3-(ethyl E-2-methyl-propenoate)]-4-(4-methoxy-phenoxy)benzene.

Light brownish oil; MS (NBA): 424 (M)$^+$

14e) The diester from 14d) was hydrolyzed according to a standard method (sodium hydroxide in methanol). Isolated: 1,2-Di[3-(E-2-methyl-propenoic acid)]-4-(4-methoxy-phenoxy)benzene.

Pale yellow solid;

Mp: 112° C.; MS (ES): 368 (M)$^+$

14f The dicarboxylic acid from 14e) was converted into the diguanidide dihydrochloride according to Variant 1 A.

Colorless solid;

Mp: 212° C.; MS (ES): 451 ((M+1)$^{+)}$

Example 15: 1,2-Bis[3-(E-2-methylpropenoic acid guanidide)]-4-(4-methyl-phenoxy)benzene dihydrochloride

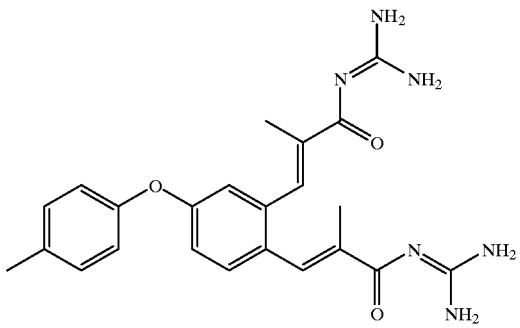

15a) Dimethyl 4-nitrophthalate was reacted in DMF with sodium 4-methylphenoxide to give dimethyl 4-(4-methylphenoxy)phthalate in analogy to a process known from the literature (J. Org. Chem. Vol. 42, No. 21, 1977, 3419–3425). After standard working up and chromatography using hexane/EA, the diester was isolated as a yellowish oil.

MS (CI): 301 ((M+1)$^+$).

15b, c) The diester 15a) was converted into the dialcohol 15b) according to a standard method (e.g. reduction with lithium aluminum hydride). The alcohol was then oxidized to the dialdehyde 15c) under standard conditions (e.g. Swern oxidation).

Dialcohol 15b): Yellowish oil; MS (CI): 244 (M$^+$), 245 ((M+1)$^+$).

Dialdehyde 15c): Brownish oil, MS (CI): 241 ((M+1)$^+$).

15d) 1 eq. of triethyl 2-phosphonopropionate was deprotonated at 0° C. using 1 eq. of n-butyllithium in hexane and then treated at RT with 0.5 eq. of 1,2-phthalaldehyde 15c). After complete reaction of the dialdehyde, the mixture was worked up using water and extracted three times by shaking with toluene. After drying the combined organic phases over magnesium sulfate, the solvent was removed in vacuo and the residual crude product was separated chromatographically on silica gel using EA/HEP mixtures as eluent. Isolated: 1,2-Di[3-(ethyl E-2-methyl-propenoate)]-4-(4-methylphenoxy)benzene.

Light brownish oil; MS (NBA): 408 (M$^+$), 409 ((M+1)$^+$)

15e) The diester from 15d) was hydrolyzed according to a standard method (sodium hydroxide in methanol). Isolated: 1,2-Di[3-(E-2-methyl-propenoic acid)]-4-(4-methylphenoxy)benzene.

Colorless solid;
Mp: 185° C.; MS (NBA): 352 (M)$^+$

15f) The dicarboxylic acid from 15e) was converted into the diguanidide dihydrochloride according to Variant 1 A.
Colorless solid;
Mp: 186° C.; MS (ES): 435 ((M+1)$^+$)

Example 16: 1,3-Bis[3-(E-2-methyl propenoic acid guanidide)]-5-methoxy-benzene hydrochloride

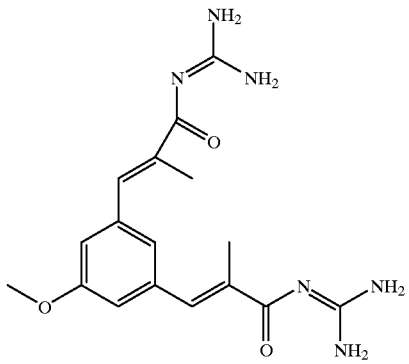

16a) 1 eq. of triethyl 2-phosphonopropionate was deprotonated at 0° C. using 1 eq. of n-butyllithium in hexane and then treated at RT with 0.5 eq. of 5-methoxy-1,3-isophthalaldehyde. After complete reaction of the dialdehyde, the mixture was worked up using water and extracted three times by shaking with toluene. After drying the combined organic phases over magnesium sulfate, the solvent was removed in vacuo and the residual crude product was separated chromatographically on silica gel using EA/HEP mixtures as eluent. Isolated: 1,3-Di[3-(ethyl E-2-methylpropenoate)]-5-methoxybenzene.

Colorless oil; MS (CI): 333 ((M+1)$^+$)

16b) The diester from 16a) was hydrolyzed according to a standard method (sodium hydroxide in methanol). Isolated: 1,3-Di[3-(E-2-methyl-propenoic acid)]-5-methoxybenzene.

Colorless solid;
Mp: >200° C.; MS (DCI): 276 (M)$^+$

16c) The dicarboxylic acid from 16b) was converted into the diguanidide according to Variant 1 A and isolated as the hydrochloride.
Colorless solid;
Mp: 124° C.; MS (NBA): 359 ((M+1)$^+$)

Example 17: 1,3-Bis[3-(E-2-methylpropenoic acid guanidide)]-5-tert-butyl-benzene hydrochloride

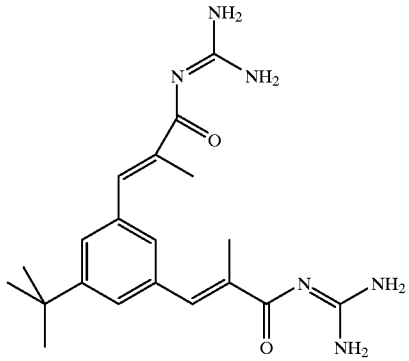

17a) 1 eq. of triethyl 2-phosphonopropionate was deprotonated at 0° C. using 1 eq. of n-butyllithium in hexane and then treated at RT with 0.5 eq. of 5-tert-butyl-1,3-isophthalaldehyde. After complete reaction of the dialdehyde, the mixture was worked up using water and extracted three times by shaking with toluene. After drying the combined organic phases over magnesium sulfate, the solvent was removed in vacuo and the residual crude product was separated chromatographically on silica gel using EA/HEP mixtures as eluent. Isolated: 1,3-Di[3-(ethyl E-2-methyl-propenoate)]-5-methoxybenzene.

Colorless oil; MS (Cl): 359 ((M+1)$^+$)

17b) The diester from 17a) was hydrolyzed according to a standard method (sodium hydroxide in methanol). Isolated: 1,3-Di[3-(E-2-methyl-propenoic acid)]-5-tert-butylbenzene.

Colorless solid;

mp: >200° C.; MS (DCl): 302 (M)+

17c) The dicarboxylic acid from 17b) was converted into the diguanidide according to Variant 1 A and isolated as the hydrochloride.

Colorless solid;

Mp: 115° C.; MS (NBA): 385 ((M+1)$^+$)

Example 18: 1,4-Bis[3-(E-2-methylpropenoic acid guanidide)]-2,5-dichlorobenzene dihydrochloride

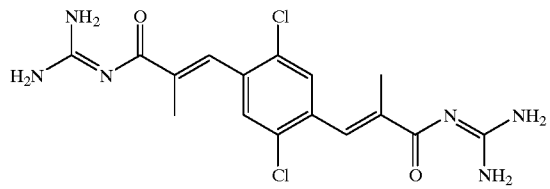

18a) 1 eq. of triethyl 2-phosphonopropionate was deprotonated at 0° C. using 1 eq. of n-butyllithium in hexane and then treated at RT with 0.5 eq. of 1,4-(2,5-dichloro) terephthalaldehyde. After complete reaction of the dialdehyde, the mixture was worked up using water and extracted three times by shaking with toluene. After drying the combined organic phases over magnesium sulfate, the solvent was removed in vacuo and the residual crude product was separated chromatographically on silica gel using EA/HEP mixtures as eluent. Isolated: 1,4-Di[3-(ethyl E-2-methyl-propenoate)]-2,5-dichlorobenzene.

Colorless solid;

Mp: amorphous; MS (DCl): 371 ((M+1)$^+$)

18b) The ester from 18a) was hydrolyzed according to a standard method (sodium hydroxide in methanol). Isolated: 1,4-Di[3-(E-2-methylpropenoic acid)]-2,5-dichlorobenzene.

Colorless solid; MS (DCl): 315 ((M+1)$^+$)

18c) The dicarboxylic acid from 18b) was converted into the diguanidide dihydrochloride according to Variant 1 A.

Yellow solid;

Mp: >200° C.; MS (DCl): 397 ((M+1)$^+$)

Example 19: 1,2-Bis[3-(E-2-methylpropenoic acid guanidide)]-4-(phenoxy)-benzene dihydrochloride.

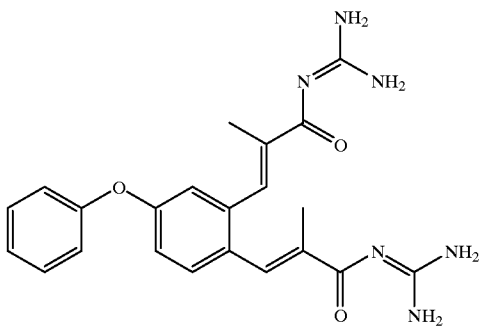

19a) Methyl 4-nitrophthalate was reacted in DMF with sodium phenoxide to give dimethyl 4-phenoxyphthalate in analogy to a process known from the literature (J. Org. Chem. Vol. 42, No. 21, 1977, 3419–3425). After standard working up and chromatography using hexane/EA, the diester was isolated as a yellowish oil.

MS (Cl): 287 ((M+1)$^+$).

19b,c) The diester 19a) was converted into the dialcohol 19b) according to a standard method (e.g. reduction with lithium aluminum hydride). The alcohol was then oxidized to the dialdehyde 19c) under standard conditions (e.g. Swern oxidation).

Dialcohol 19b): Yellowish oil; MS (Cl): 230 (M$^+$), 231 ((M+1)$^+$).

Dialdehyde 19c): Brownish oil, MS (Cl): 227 ((M+1)$^+$).

19d) 1 eq. of triethyl 2-phosphonopropionate was deprotonated at 0° C. using 1 eq. of n-butyllithium in hexane and then treated at RT with 0.5 eq. of 1,2-phthalaldehyde 19c). After complete reaction of the dialdehyde, the mixture was worked up using water and extracted three times by shaking with toluene. After drying the combined organic phases over magnesium sulfate, the solvent was removed in vacuo and the residual crude product was separated chromatographically on silica gel using EA/HEP mixtures as eluent. Isolated: 1,2-Di[3-(ethyl E-2-methyl-propenoate)]A (phenoxy) benzene.

Light brownish oil; MS (NBA): 394 (M)$^+$, 395 ((M+1 )$^+$)

19e) The diester from 19d) was hydrolyzed according to a standard method (sodium hydroxide in methanol). Isolated: 1,2-Di[3-(E-2-methyl-propenoic acid)]-4-(phenoxy) benzene.

Colorless solid;

Mp: 160° C.; MS (NBA): 338 (M)$^+$

19f) The dicarboxylic acid from 19e) was converted into the diguanidide dihydrochloride according to Variant 1 A.

Colorless solid;

Mp: 170° C.; MS (ES): 421 ((M+1)$^+$)

Example 20: 1,2-Bis[3-(E-2-methylpropenoic acid guanidide)]-4-(methoxy)-benzene dihydrochloride

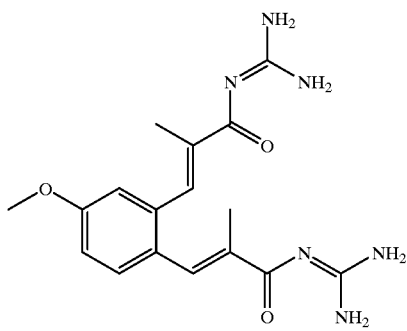

In analogy to Example 19, Example 20 was prepared by nucleophilic aromatic substitution of the 4-nitrophthalic acid ester with sodium methoxide, then reduction/oxidation/olefination reaction, hydrolysis and guanidation of the diacid.

20a) 4-Methoxyphthalic acid diester +MS(Cl): 225 ((M+1)$^+$).

Dialcohol 20b): Yellow-brownish oil; MS (Cl): 169 ((M+1)$^+$).

Daldehyde 20c): Dark oil, MS (Cl): 165 ((M+1)$^+$).

Diester 20d): Dark oil; MS (NBA): 333 ((M+1)$^+$)

20e) 1,2-Di[3-(E-2-methylpropenoic acid]-4-(methoxy) benzene

Colorless solid;

Mp: >200° C.; MS (NBA): 276 (M)$^+$

20f) The dicarboxylic acid from 20e) was converted into the diguanidide dihydrochloride according to Variant 1 A.

Colorless solid

Mp: 170° C.; MS (ES): 359 ((M+1)$^+$)

Example 21: 1,2-Bis[3-(E-2-methylpropenoic acid guanidide)]-4-(ethoxy) benzene dihydrochloride

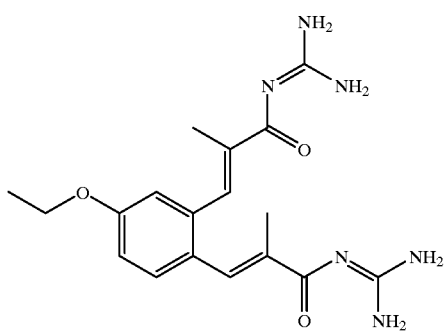

21a) Diethyl 4-ethoxyphthalate was prepared by ethylation of 4-hydroxyphthalic acid using 3.5 equivalents of ethyl iodide and 3.1 equivalents of potassium carbonate in DMF at 70° C. Via reduction/oxidation/olefination reaction, the diester was then prepared, which was converted into the diguanidide 21 according to Variant 1 B.

21a) Diethyl 4-ethoxyphthalate; dark oil; MS (Cl): 267 ((M+1)$^+$). Dialcohol 21b): Yellow-brownish oil; MS (Cl): 183 ((M+1)$^+$).

Dialdehyde 21c): Dark oil, MS (Cl): 179 ((M+1)$^+$).

Diester 21d): Yellowish oil; MS (NBA): 347 ((M+1)$^+$)

21f The diester 20d) was converted into the diguanidide dihydrochloride according to Variant 1 B.

Colorless solid;

Mp: 245° C.; MS (ES): 373 ((M+1)$^+$)

Example 22: 1,2-Bis[3-(E-2-methylpropenoic acid guanidide]-4-(3-pyridyloxy)benzene dihydrochloride

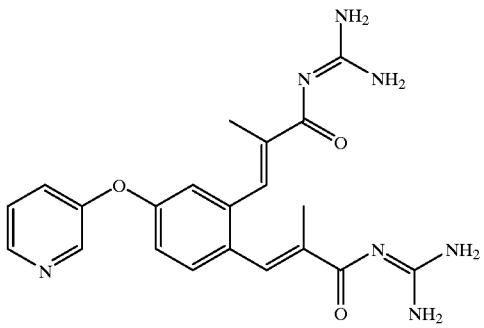

22a) Dimethyl 4-nitrophthalate was reacted in DMF with 3-hydroxypyridine sodium salt in analogy to a process known from the literature (J. Org. Chem. Vol. 42, No. 21, 1977, 3419–3425) to give dimethyl 4-(3-pyridyloxy) phthalate. After standard working up and chromatography using hexane/EA, the diester was isolated as a yellowish oil.

MS: 288 ((M+1)$^+$).

22b,c) The diester 22a) was converted into the dialcohol 22b) according to a standard method (e.g. reduction with lithium aluminum hydride). The alcohol was then oxidized to the dialdehyde 22c) under standard conditions (e.g. Swern oxidation).

Dialcohol 22b): Yellowish oil; MS: 232 ((M+1)$^+$).

Dialdehyde 22c): Yellow-brownish oil; MS: 228 ((M+1)$^+$).

22d) 1 eq. of triethyl 2-phosphonopropionate was deprotonated at 0° C. using 1 eq. of n-butyllithium in hexane and then treated at RT with 0.5 eq. of 1,2-phthalaldehyde 22c). After complete reaction of the dialdehyde, the mixture was worked up using water and extracted three times by shaking with toluene. After drying the combined organic phases over magnesium sulfate, the solvent was removed in vacuo and the residual crude product was separated chromatographically on silica gel using EA/HEP mixtures as eluent. Isolated: 1,2-Di[3-(ethyl E-2-methyl-propenoate)]-4-(3-pyridyloxy)benzene.

Light brownish oil; MS: 396 ((M+1)$^+$)

22e) The diester from 22d) was hydrolyzed according to a standard method (sodium hydroxide in methanol). Isolated: 1,2-Di[3-(E-2-methyl-propenoic acid)-A-(3-pyriyloxy)benzene.

Colorless solid;

Mp: 210° C.; MS: 339 (M)$^+$

22f) The dicarboxylic acid from 22e) was converted into the diguanidide dihydrochloride according to Variant 1 A.

Colorless solid;

Mp: 176° C.; MS: 422 ((M+1)$^+$)

Example 23: 1,2-Bis[3-(E-2-methylpropenoic acid guanidide]-4-[4-(2-dimethylaminoethylene)phenoxy]benzene dihydrochloride

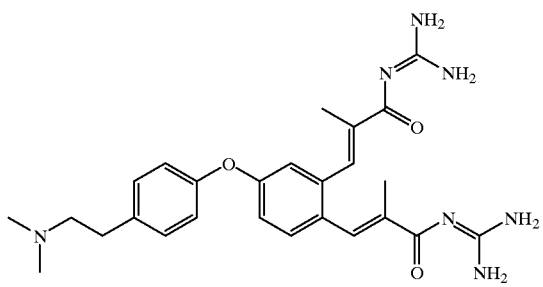

23a) Dimethyl 4-nitrophthalate was reacted in DMF with sodium 4-(2-dimethylaminoethylene)phenoxide to give dimethyl 4-[4-(2-dimethylamino-ethylene)phenoxy]phthalate in analogy to a process known from the literature (J. Org. Chem. Vol. 42, No. 21, 1977, 3419–3425). After standard working up and chromatography using hexane/EA, the diester was isolated.

MS: 358 ((M+1)$^+$)

23b,c) The diester 23a) was converted into the dialcohol 23b) according to a standard method (reduction using lithium aluminum hydride). The alcohol was then oxidized to the dialdehyde 23c) according to Dess-Martin (see Dess-Martin oxidation; JOC, 1994, 59, 7549–7552).

Dialcohol 23b): Yellow-brown oil; MS: 340 ((M+1)$^+$).

Dialdehyde 23c) Yellow oil; MS: 269 ((M+1)$^+$).

23d) 1 eq. of triethyl 2-phosphonopropionate was deprotonated at 0° C. using 1 eq. of n-butyllithium in hexane and then treated at RT with 0.5 eq of 1,2-phthalaldehyde 23c). After complete reaction of the dialdehyde, the mixture was worked up using water and extracted three times by shaking with toluene. After drying the combined organic phases over magnesium sulfate, the solvent was removed in vacuo and the residual crude product was separated chromatographically on silica gel using EA/HEP mixtures as eluent.

Isolated: 1,2-Bis[3-(ethyl E-2methylpropenoate)]-4-[4-(2-dimethylamino-ethylene)phenoxy]benzene.

Yellowish oil; MS: 466 ((M+1)$^+$).

23e) The diester from 23d) was hydrolyzed according to a standard method (sodium hydroxide in methanol). Isolated: 1,2-Bis[3-(E-2-methyl-propenoic acid)]-4-[4-(2-dimethylaminoethylene)phenoxy]benzene.

Colorless solid;

Mp:>220° C.: MS: 409 (M)$^+$

23f) The dicarboxylic acid from 23e) was converted into the diguanidide dihydrochloride according to Variant 1 A. MS: 410 ((M+1)$^+$)

Examples 24 and 25: 1,2-Bis[3-(E-2-methylpropenoic acid guanidide)]-4-[4-methoxybenzyloxy]benzene dihydrochloride and 1,2-Bis[3-(E-2-methylpropenoic acid guanidide)]-4-hydroxybenzene dihydrochloride

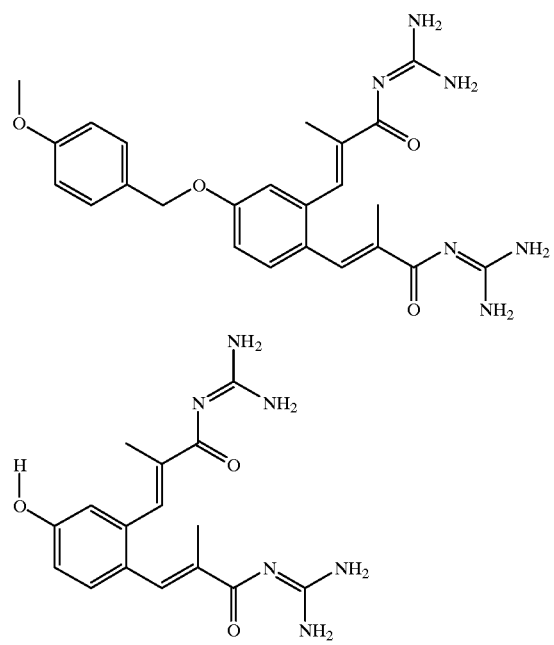

24a) 1 eq. of dimethyl 4-hydroxyphthalate, 1.1 eq. of potassium carbonate and 1.1 eq. of 4-methoxybenzyl chloride were stirred in DMF at RT. After 4 days, the mixture was worked up according to a standard procedure. Dimethyl 4-(4-methoxybenzyloxy)phthalate was isolated as a colorless oil. MS: 331 ((M+1)$^+$)

24b, c) The diester 24a) was converted into the dialcohol 24b) according to a standard method (reduction with lithium aluminum hydride). The alcohol was then oxidized to the dialdehyde 24c) according to a standard procedure (Swern oxidation).

Dialcohol 24b): Amorphous solid; MS: 275 ((M+1)$^+$).

Dialdehyde 24c): Yellowish oil, MS: 271 ((M+1)$^+$).

24d) 1 eq. of triethyl 2-phosphonopropionate was deprotonated at 0° C. using 1 eq. of n-butyllithium in hexane and then treated at RT with 0.5 eq. of 1,2-phthalaldehyde 24c). After complete reaction of the dialdehyde, the mixture was worked up using water and extracted three times by shaking with toulene. After drying the combined organic phases over magnesium sulfate, the solvent was removed in vacuo and the residual crude product was separated chromatographically on silica gel using EA/HEP mixtures as eluent.

Isolated: 1,2-Bis[3-(methyl E-2-methylpropenoate)]-4-[4-methoxybenzyloxy]benzene, as a yellowish oil. MS: 439 ((M+1)$^+$)

24e) The diester from 24d) was hydrolyzed according to a standard method (sodium hydroxide in methanol). Isolated: 1,2-Bis[E-2-methylpropenoic acid)]-4-[4-methoxybenzyloxy]benzene, colorless solid.

Mp. 206–220° C.; MS: 382 (M)$^+$

24f) The dicarboxylic acid from 24e) was converted into the diguanidide dihydrochloride according to Variant 1 A.

Mp. 210° C.; MS: 465 ((M+1)$^+$)

Example 25: 1,2-Bis[3-(E-2-methylpropenoic acid guanidide)]-4-hydroxy-benzene dihydrochloride The dicarboxylic acid from 24e) was reacted to give the diguanidide dihydrochloride according to Variant 1 A. In addition to Example 24, the product 25 was isolated. MS: 345 ((M+1)$^+$).

Pharmacological data:

Inhibitors of the Na$^+$/H+ exchanger of rabbit erythrocytes (subtype 1; NHE-1):

White New Zealand rabbits (Ivanovas) received a standard diet with 2% cholesterol for six weeks in order to activate the Na$^+$/H$^+$ exchange and thus to be able to determine the Na$^+$ influx into the erythrocytes via Na$^+$/H$^+$ exchange by flame photometry. The blood was taken from the auriular arteries and rendered incoagulable by means of 25 IU/ml of potassium heparin. A part of each sample was used for the duplicate determination of the hematocrit by centrifugation. Aliquots of 100 μl in each case were used to measure the Na$^+$ starting content of the erythrocytes.

In order to determine the amiloride-sensitive sodium influx, 100 μl of each blood sample in 5 ml in each case of a hyperosmolar salt-sucrose medium (mmol/l: 140 NaCl, 3 KCl, 150 sucrose, 0.1 ouabain, 20 trishydroxymethylaminomethane) were incubated at pH 7.4 and 37° C.

The erythrocytes were then washed three times with ice-cold MgCl$_2$-ouabain solution (mmol/l: 112 MgCl$_2$, 0.1 ouabain) and hemolyzed in 2.0 ml of distilled water. The intracellular sodium content was determined by flame photometry.

The Na$^+$ net influx was calculated from the difference between sodium starting values and the sodium content of the erythrocytes after incubation. The amiloride-inhibitable sodium influx resulted from the difference in the sodium content of the erythrocytes after incubation with and without amiloride 3×10$^{-4}$ mol/l. The procedure was also carried out in the same manner in the case of the compounds according to the invention.

Results of the inhibition of the Na$^+$/H$^+$ exchanger (subtype 1; NHE-1):

| Example (see exp. section) | IC$_{50}$ (μmol) |
|---|---|
| 4 | 4 |

Most molecular biology techniques follow protocols from the works Current Protocols in Molecular Biology (eds. Ausubel, F. M., Brent, R., Kingston, H. E., Moore, D. D., Seidman, J. G., Smith, J. A. and Struhl, K.; John Wiley & Sons) or Molecular Cloning: A Laboratory Manual (Sambrock, J., Fritsch, E. F. and Maniatis, T.; Cold Spring Harbor Laboratory Press (1989)). In our studies, stable transfected cell lines were produced which in each case express one of the following NHE subtypes: NHE1 of man (Sardet et al.; Cell 56, 271–280 (1989), NHE2 of the rabbit (Tse et al.; J. Biol. Chem. 268, 11917–11924(1993)) or NHE3 of the rat (Orlowski et a.; J. Biol. Chem. 267, 9331–9339 (1992)).

After adding suitable linker sequences, the cDNA clones of the respective NHE subtypes obtained by Prof. Pouysségur were cloned into the expression plasmid pMAMneo (obtainable, for example, via CLONTECH, Heidelberg) such that the NHE1 recognition sequence of the plasmid is approximately 20–100 base pairs before the start codon: of the respective NHE subtype and the entire coding sequence is present in the construct. Using the so-called "calcium phosphate method" (described in Chapter 9.1 of "Protocols in Molecular Biology"), the NHE-deficient cell line LAP1 (Franchi et al.; Proc. Nat. Acad. Sci. USA 83, 9388–9392 (1986)) was transfected with the plasmids which contain the respective coding sequences of the NHE subtypes. After selection of transfected cells by means of growth in G418-containing medium (only cells which as a result of transfection contain a neogene can survive under these conditions), a selection was made for functional NHE expression. To do this, the "Acid Load" technique described by Sardet was used (Sardet et al.; Cell 56, 271–280 (1989)). Cells which express a functioning NHE subtype can also compensate in the absence of CO$_2$ and HCO$_3$- for the acidification carried out during this test, but untransfected LAP1 cells cannot. After repetition of the "Acid Load" selection several times, the surviving cells were inoculated into microtiter plates such that statistically there should be one cell per well. Under the microscope, a check was made after approximately 10 days as to how many colonies were growing per well. Cell populations of individual colonies were then investigated with respect to their viability anger "Acid Load" using the X-II-T proliferation kit (Boehringer Mannheim). The best cell lines ware used for the further tests and to avoid a loss of the transtected sequence were cultured under continuous selection pressure in G418-containing medium.

To determine IC$_{50}$-values for the inhibition of the individual NHE subtypes by specific substances, a test developed by S. Faber (Faber et al.; Cell. Physiol. Biochem. 6, 39–49 (1996)), which is based on the "Acid Load" technique, was slightly modified.

In the test used, the recovery of the intracellular pH (pH$_i$) after an acidification was determined, which commences with functioning NHE even under bicarbonate-free conditions. To do this, the pH$_i$ was determined using the pH-sensitive fluorescent dye BCECF (Calbiochem, the precursor BCECFAM) was employed). The cells were first loaded with BCECF. The BCECF fluorescence was determined in a "Ratio Fluorescence Spectrometer" (Photon Technology International, South Brunswick, N.J., USA) at excitation wavelengths of 505 and 440 nm and an emission wavelength of 535 nm and converted into the pH$_i$ by means of calibration curves. Differing from the protocol described, the cells were incubated in NH$_4$Cl-buffer (pH 7.4) even during the BCECF loading (NH$_4$Cl buffer: 115 mM NaCl, 20 mM NH$_4$Cl, 5 mM KCl, 1 mM CaCl$_2$, 1 mM MgSO$_4$, 20 mM HEPES, 5 mM glucose, 1 mg/ml BSA; a pH of 7.4 is established using 1M NaOH). The intracellular acidification was induced by addition of 975 μl of an NH$_4$Cl-free buffer to 25 μl aliquots of the cells incubated in NH$_4$Cl buffer. The subsequent rate of the pH recovery was recorded as 2 minutes in the case of NHE1, as 5 minutes in the case of NHE2, and as 3 minutes in the case of NHE3. To calculate the inhibitory potency of the substances tested, the cells were first investigated in buffers in which a complete pH recovery or no pH recovery at all took place. For the complete pH recovery (100%), the cells were incubated in Na-containing buffer (133.8 mM NaCl, 4.7 mM KCl, 1.25 mM CaCl$_2$, 1.25 mM MgCl$_2$, 0.97 mM Na$_2$HPO$_2$, 0.23 mM NaH$_2$PO$_4$, 5 mM HEPES, 5 mM glucose, a pH of 7.0 is established using 1M NaOH). For the determination of the 0% value, the cells were incubated in an Na$^+$-free buffer (133.8 mM choline chloride, 4.7 mM KCl, 1.25 mM CaCl$_2$, 1.25 mM MgCl$_2$, 0.97 mM K$_2$HPO$_4$, 0.23 mM KH$_2$PO$_4$, 5 mM HEPES, 5 mM glucose, a pH of 7.0 is established using 1M NaOH). The substances to be tested were prepared in the Na$^+$-containing buffer. The recovery of the intracellular pH at each tested concentration of a substance was expressed in percent of the maximum recovery. From the percentage values of the pH recovery, the $IC_{50}$ value of the particular substance for the individual NHE subtypes was calculated by means of the program SigmaPlot

|  | $IC_{50}$; NHE-3 |
|---|---|
| Example 1 | 0.7 |
| Example 6 | 3.2 |
| Example 9 | 1.75 |
| Example 3 | 1.1 |

What is claimed is:

1. A phenyl-substituted alkenylcarboxylic acid guanidide of the formula I:

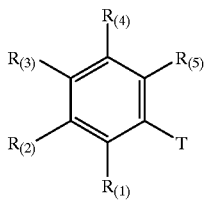

in which:

T is

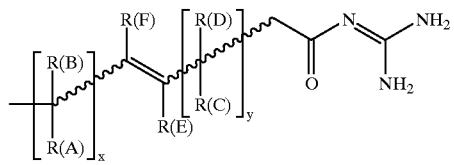

wherein

R(A) is hydrogen, F, Cl, Br, I, CN, OH, OR(6), $(C_1-C_4)$-alkyl, $O_r(CH_2)_aC_bF_{2b+1}$, $(C_3-C_8)$-cycloalkyl or N R(7) R(8);

r is zero or 1;

a is zero, 1, 2, 3 or 4;

b is 1, 2, 3 or 4;

R(6) is $(C_1-C_4)$-alkyl, $(C_1-C_4)$-perfluoroalkyl, $(C_3-C_6)$-alkenyl, $(C_3-C_8)$-cycloalkyl, phenyl or benzyl, the phenyl nucleus being unsubstituted or substituted by 1–3 substituents selected from the group consisting of F, Cl, $CF_3$, methyl, methoxy and NR(9)R(10);

R(9) and R(10) are H, $(C_1-C_4)$-alkyl or $(C_1-C_4)$-perfluoroalkyl;

R(7) and R(8) independently of one another are defined as R(6);

or

R(7) and R(8) together are 4 or 5 methylene groups, of which one $CH_2$ group can be replaced by oxygen, sulfur, NH, N—$CH_3$ or N-benzyl;

R(B), R(C) and R(D) independently are defined as R(A);

x is zero, 1 or 2;

y is zero, 1 or 2;

R(F) is hydrogen, F, Cl, Br, I, CN, OR(12), $(C_1-C_8)$-alkyl, $O_p(CH_2)_fC_gF_{2g+1}$, $(C_3-C_8)$-cycloalkyl or $(C_1-C_9)$-heteroaryl;

p is zero or 1;

f is zero, 1, 2, 3 or 4;

g is 1, 2, 3, 4, 5, 6, 7 or 8;

R(12) is $(C_1-C_8)$-alkyl, $(C_1-C_4)$-perfluoroalkyl, $(C_3-C_8)$-alkenyl, $(C_3-C_8)$-cycloalkyl, phenyl or benzyl, the phenyl nucleus being unsubstituted or substituted by 1–3 substituents selected from the group consisting of F, Cl, $CF_3$, methyl, methoxy and NR(13)R(14);

R(13) and R(14) are H, $(C_1-C_4)$-alkyl or $(C_1-C_4)$-perfluoroalkyl;

R(E) is defined as R(F);

R(1) is defined as T;

or

R(1) is hydrogen, $-O_kC_mH_{2m+1}$, $-O_n(CH_2)_pC_qF_{2q+1}$, F, Cl, Br, I, CN, $-(C=O)-N=C(N H_2)_2$, $-SO_rR(17)_1$, $-SO_{r2}NR(31)R(32)$, $-O_u(CH_2)_vC_6H_5$, $-O_{u2}-(C_1-C_9)$-heteroaryl or $-S_{u2}-(C_1-C_9)$-heteroaryl;

k is zero or 1;

m is zero, 1, 2, 3, 4, 5, 6, 7 or 8;

n is zero or 1;

p is zero, 1, 2, 3 or 4;

q is 1, 2, 3, 4, 5, 6, 7 or 8;

r is zero, 1, 2;

r2 is zero, 1 or 2;

R(31) and R(32) independently of one another are hydrogen, $(C_1-C_8)$-alkyl or $(C_1-C_8)$-perfluoroalkyl;

or

R(31) and R(32) are together 4 or 5 methylene groups, one of which can be substituted by oxygen, S, NH, N—$CH_3$ or N-benzyl;

R(17) is $(C_1-C_8)$-alkyl;

u is zero or 1;

u2 is zero or 1;

v is zero, 1, 2, 3 or 4;

the phenyl nucleus being unsubstituted or substituted by 1–3 substituents selected from the group consisting of F, Cl, $CF_3$, methyl, methoxy, $-(CH_2)_wNR(21)R(22)$, NR(18)R(19) and $(C_1-C_9)$-heteroaryl;

R(18), R(19), R(21) and R(22) independently of one another are $(C_1-C_4)$-alkyl or $(C_1-C_4)$-perfluoroalkyl;

w is 1, 2, 3 or 4;

the heterocycle of the $(C_1-C_9)$-heteroaryl being unsubstituted or substituted by 1–3 substituents selected from the group consisting of F, Cl, $CF_3$, methyl and methoxy;

R(2), R(3), R(4) and R(5) independently of one another are defined as $R_{(1)}$; or R(1) and R(2) or R(2) and R(3) in each case together are —CH—CH=CH—CH—, which is unsubstituted or is substituted by 1–3 substituents selected from the group consisting of F, Cl, $CF_3$, methyl, methoxy, $-(CH_2)_{w2}NR(24)R(25)$ and NR(26)R(27);

R(24), R(25), R(26) and R(27) are H, $(C_1-C_4)$-alkyl or $(C_1-C_4)$-perfluoroalkyl;

w2 is 1, 2, 3 or 4;

wherein the radical T is present in the compound at least twice, but only three times at most; or a pharmaceutically acceptable salt thereof.

2. A compound of the formula I as claimed in claim 1, in which T is

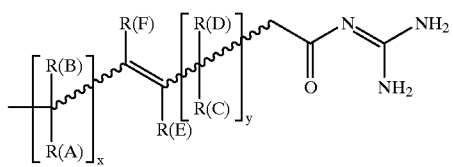

wherein
R(A) is hydrogen, F, Cl, CN, OH, OR(6), $(C_1-C_4)$-alkyl, $O_r(CH_2)_aC_bF_{2b+1}$, $(C_3-C_8)$-cycloalkyl or NR(7)R(8);
r is zero or 1;
a is zero, 1 or 2;
b is zero, 1, 2, 3 or 4;
R(6) is $(C_1-C_4)$-alkyl, $(C_1-C_4)$-perfluoroalkyl, phenyl or benzyl, the phenyl nucleus being unsubstituted or substituted by 1–3 substituents selected from the group consisting of F, Cl, $CF_3$, methyl, methoxy and NR(9)R(10);
R(9) and R(10) independently of one another are H, $CH_3$ or $CF_3$;
R(7) and R(8) independently of one another are defined as R(6);
or
R(7) and R(8) together are 4 or 5 methylene groups, of which one $CH_2$ group can be replaced by oxygen, sulfur, NH, N—$CH_3$ or N-benzyl;
R(B), R(C), R(D) independently are defined as R(A);
x is zero or 1;
y is zero or 1;
R(F) is hydrogen, F, Cl, CN, OR(12), $(C_1-C_4)$-alkyl, $O_p(CH_2)_fC_gF_{2g+1}$, $(C_3-C_8)$-cycloalkyl or $(C_1-C_9)$-heteroaryl;
p is zero or 1;
f is zero, 1 or 2;
g is 1, 2, 3 or 4;
R(12) is $(C_1-C_4)$-alkyl, $(C_1-C_4)$-perfluoroalkyl, $(C_3-C_8)$-cycloalkyl, phenyl or benzyl, the phenyl nucleus being unsubstituted or substituted by 1–3 substituents selected from the group consisting of F, Cl, $CF_3$, methyl, methoxy and NR(13)R(14);
R(13) and R(14) independently of one another are H, $CH_3$ or $CF_3$; R(E) is defined as R(F);
R(1) is defined as T;
or
R(1) is hydrogen, —$O_kC_mH_{2m+1}$, —$O_nC_qF_{2q+1}$, F, Cl, Br, I, CN, —(C=O)—N=C(NH$_2$)$_2$, —So$_r$R(17), —SO$_{r2}$NR(31)R(32), —$O_u$(CH$_2$)$_v$C$_6$H$_5$, —$O_{u2}$—$(C_1-C_9)$-heteroaryl or —$S_{u2}(C_1-C_9)$-heteroaryl;
k is zero or 1;
m is zero, 1, 2, 3 or 4;
n is zero or 1;
q is 1, 2, 3 or 4;
r is 2;
r2 is zero, 1 or 2;
R(31) and R(32) independently of one another are hydrogen, $(C_1-C_4)$-alkyl or $(C_1-C_4)$-perfluoroalkyl;
or
R(31) and R(32) are together 4 or 5 methylene groups, one of which can be replaced by oxygen, S, NH, N—$CH_3$ or N-benzyl;
R(17) is $(C_1-C_4)$-alkyl;
u is zero or 1;
u2 is zero or 1;
v is zero, 1 or 2;

the phenyl nucleus being unsubstituted or substituted by 1–3 substituents selected from the group consisting of F, Cl, $CF_3$, methyl, methoxy, —(CH$_2$)$_w$NR(21)R(22)NR(18)R(19) and $(C_1-C_9)$-heteroaryl;
R(18), R(19), R(21) and R(22) are H, $(C_1-C_4)$-alkyl or $(C_1-C_4)$-perfluoroalkyl;
w is 1, 2, 3, 4;
the heterocycle of the $(C_1-C_9)$-heteroaryl being unsubstituted or substituted by 1–3 substituents selected from the group consisting of F, Cl, $CF_3$, methyl and methoxy;
R(2), R(3), R(4) and R(5) independently of one another are defined as R(1);
or
R(1) and R(2) or R(2) and R(3) in each case together are —CH—CH=CH—CH—, which is unsubstituted or is substituted by 1–3 substituents selected from the group consisting of F, Cl, $CF_3$, methyl, methoxy, —(CH$_2$)$_{w2}$NR(24)R(25) and NR(26)R(27);
R(24), R(25), R(26) and R(27) are H, $CH_3$ or $CF_3$;
w2 is 1, 2, 3 or 4;
wherein the radical T is only present twice in the compound.
3. A compound of the formula I as claimed in claim 1, in which T is

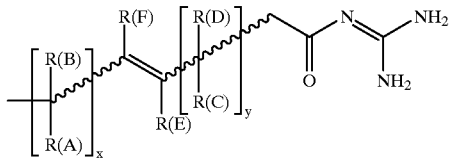

x is zero;
y is zero;
R(F) is hydrogen, F, Cl, CN, OR(12), $(C_1-C_4)$-alkyl, —$O_pC_gF_{2g+1}$, $(C_3-C_8)$-cycloalkyl or $(C_1-C_9)$-heteroaryl;
p is zero or 1;
g is 1, 2, 3 or 4;
R(12) is $(C_1-C_4)$-alkyl, $CF_3$, $(C_3-C_8)$-cycloalkyl, phenyl or benzyl, the phenyl nucleus in each case being unsubstituted or substituted by 1–3 substituents selected from the group consisting of F, Cl, $CF_3$, methyl, methoxy and NR(13)R(14);
R(13) and R(14) are H, $CH_3$ or $CF_3$;
R(E) is defined as R(F);
R(1) is defined as T;
or
R(1) is hydrogen, —$O_kC_mH_{2m+1}$, $O_nC_qF_{2q+1}$, F, Cl, CN, —(C=O) N=C(NH$_2$)$_2$, —SO$_2$CH$_3$, —SO$_2$NR(31)R(32), —$O_u$(CH$_2$)$_v$C$_6$H$_5$, —$O_{u2}$—$(C_1-C_9)$-heteroaryl or —$S_{u2}$—$(C_1-C_9)$-heteroaryl;
k is zero or 1;
m is zero, 1, 2, 3 or 4;
n is zero or 1;
q is 1, 2, 3 or 4;
R(31) and R(32) independently of one another are hydrogen or $(C_1-C_4)$-alkyl;
or
R(31) and R(32) are together 4 or 5 methylene groups, one of which can be replaced by oxygen, S, NH, N—$CH_3$ or N-benzyl;
u is zero or 1;
u2 is zero or 1;

v is zero or 1;

the phenyl nucleus being unsubstituted or substituted by 1–3 substituents selected from the group consisting of F, Cl, CF$_3$, methyl, methoxy, —(CH$_2$)$_w$NR(21)R(22) and NR(18)R(19);

R(18), R(19), R(21) and R(22) independently of one another are H, (C$_1$–C$_4$)-alkyl or (C$_1$–C$_4$)-perfluoroalkyl;

w is 1, 2, 3 or 4;

the heterocycle of the (C$_1$–C$_9$)-heteroaryl being unsubstituted or substituted by 1–3 substituents selected from the group consisting of F, Cl, CF$_3$, methyl and methoxy;

R(2), R(3), R(4) and R(5) independently of one another are defined as R(1);

or

R(1) and R(2) or R(2) and R(3) in each case together are —CH—CH═CH—CH—, which is unsubstituted or is substituted by 1–3 substituents selected from the group consisting of F, Cl, CF$_3$, methyl, methoxy, (CH$_2$)$_{w2}$NR(24)R(25) and NR(26)R(27);

R(24), R(25), R(26) and R(27) independently of one another are H, (C$_1$–C$_4$)-alkyl or (C$_1$ –C$_4$)-perfluoroalkyl;

w2 is 1, 2, 3 or 4;

wherein the radical T is only present twice in the compound.

4. A compound of the formula I as claimed in claim 1, said compound being:

1,2-Bis[3-(E-2-methylpropenoic acid guanidide)]benzene dihydrochloride, 1,3-Bis[3-(E-2-methylpropenoic acid guanidide)]benzene dihydrochloride, 1,4-Bis[3-(E-2-methylpropenoic acid guanidide)]benzene dihydrochloride, 2,3-Bis[3-(E-2-methylpropenoic acid guanidide)] naphthalene dihydrochloride, 1,2-Bis[3-(Z-2-fmuoropropenoic acid guanidide)]benzene dihydrochloride, 1-[3-(Z-2-fluoropropenoic acid guanidide)]-2-[-(E-2-methylpropenoic acid guanidide)]benzene dihydrochloride, 1,3-Bis[3-(Z-2-fluoropropenoic acid guanidide)]benzene dihydrochloride, 1,3-Bis[3-(E-2-methylpropenoic acid guanidide)]-2-methoxy-5-methyl-benzene hydrochloride, 1,2-Bis[3-(E-2-methylpropenoic acid guanidide)]-4-methylbenzene dihydrochide, 1,2-Bis[3-(E-2-methylpropenoic acid guanidide)]-4,5-dichlorobenzene dihydrochloride, 1,3-Bis[3-(E-propenoic acid guanidide)]benzene dihydrochloride, 1,2-Bis[3-(E-2-methylpropenoic acid guanidide)]-4-bromobenzene dihydrochloride, 1,2-Bis[3-(E-2-methylpropenoic acid guanidide)]-4-(4-methoxyphenoxy)-benzene dihydrochloride, 1,2-Bis[3-(E-2-methylpropenoic acid guanidide)]-4-(4-methylphenoxy)-benzene dihydrochloride, 1,3-Bis[3-(E-2-methylpropenoic acid guanidide)]-5-methoxybenzene hydrochloride, 1,3-Bis[3-(E-2-methylpropenoic acid guanidide)]-5-tert-butylbenzene hydrochloride, 1,4-Bis[3-(E-2-methylpropenoic acid guanidide)]-2,5-dichlorobenzene dihydrochloride, 1,2-Bis[3-(E-2-methylpropenoic acid guanidide)]-4-(phenoxy)benzene dihydrochloride, 1,2-Bis[3-(E-2-methylpropenoic acid guanidide)]-4-(methoxy)benzene dihydrochloride, 1,2-Bis[3-(E-2-methylpropenoic acid guanidide)]-4-(ethoxy)benzene dihydrochloride or 1,2-Bis[3-(E-2-methylpropenoic acid guanidide)]-4-(3-pyridyloxy)benzene dihydrochloride.

5. A process for the preparation of a compound of formula I according to claim 1, said process comprising reacting a compound of the formula II

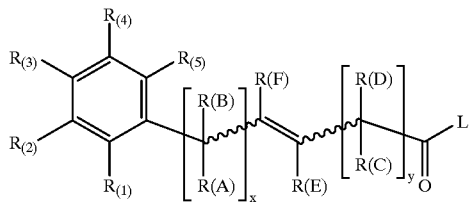

in which R(1), R(2), R(3), R(4), R(5), R(A), R(B), R(C), R(D), R(E), R(F), x and y are defined as in claim 1, and L is an easily nucleophilically substitutable leaving group, with guanidine.

6. A pharmaceutical composition for treating arrhythmias, which comprises an effective amount of a compound of formula I or a pharmaceutically acceptable salt thereof as claimed in claim 1 together with a pharmaceutically acceptable carrier.

7. A method for treating or preventing arrhythmias, which comprises administering to a host in need of said treatment an effective amount of a compound of formula I or a salt thereof as claimed in claim 1.

8. A method for treating or preventing cardiac infarct, which comprises administering to a host in need of said treatment an effective amount of a compound of formula I or a salt thereof as claimed in claim 1.

9. A method for treating or preventing angina pectoris, which comprises administering to a host in need of said treatment an effective amount of a compound of formula I or a salt thereof as claimed in claim 1.

10. A method for treating or preventing ischemic conditions of the heart, which comprises administering to a host in need of said treatment an effective amount of a compound of formula I or a salt thereof as claimed in claim 1.

11. A method for treating or preventing ischemic conditions of the peripheral and central nervous system and of stroke, which comprises administering to a host in need of said treatment an effective amount of a compound of formula I or a salt thereof as claimed in claim 1.

12. A method for treating or preventing ischemic conditions of peripheral organs and members, which comprises administering to a host in need of said treatment an effective amount of a compound of formula I or a salt thereof as claimed in claim 1.

13. A method for treating or preventing states of shock, which comprises administering to a host in need of said treatment an effective amount of a compound of formula I or a salt thereof as claimed in claim 1.

14. A pharmaceutical composition for use in surgical operations and organ transplantation, which comprises an effective amount of a compound of formula I or a salt thereof as claimed in claim 1 and a pharmaceutically acceptable carrier.

15. A pharmaceutical composition for use in preserving and storing procedures, which comprises an effective amount of a compound of formula I or a salt thereof as claimed in claim 1 and a pharmaceutically acceptable carrier.

16. A method of treating or preventing diseases in which cell proliferation is a primary or secondary cause, which comprises administering to a host in need of said treatment an effective amount of a compound of formula I or salt thereof as claimed in claim 1.

17. A method of treating or preventing disorders of lipid metabolism, which comprises administering to a host in need of said treatment an effective amount of a compound of formula I or a salt thereof as claimed in claim 1.

18. A method of treating or preventing impaired respiratory drive, which comprises administering to a host in need of said treatment an effective amount of a compound of formula I or a salt thereof as claimed in claim 1.

19. A diagnostic agent for inhibiting the Na+/H+ exchanger and for diagnosing hypertension, atherosclerosis, diabetes and proliferative disorders, which comprises an effective amount of a compound of formula I or a salt thereof as claimed in claim 1.

20. A method of treating or preventing acute or chronic kidney failure, which comprises administering to a host in need of said treatment an effective amount of a compound of formula I or a salt thereof as claimed in claim 1.

21. A pharmaceutical composition for treating or preventing (1) cardiac infarct, (2) angina pectoris, (3) ischemic conditions of the heart, the peripheral and central nervous system, of stroke, of the peripheral organs and members, (4) states of shock, (5) diseases in which cell proliferation is a primary or secondary cause, (6) disorders of lipid metabolism, (7) impaired respiratory drive, and (8) acute or chronic kidney disorders, which comprises an effective amount of a compound of formula I as claimed in claim 1 or a salt thereof together with a pharmaceutically acceptable carrier.

* * * * *

UNITED STATES PATENT AND TRADEMARK OFFICE
CERTIFICATE OF CORRECTION

PATENT NO.    : 6,005,010
DATED         : December 21, 1999
INVENTOR(S)   : Schwark et al.

It is certified that error appears in the above-identified patent and that said Letters Patent is hereby corrected as shown below:

Title page,
Item [57], ABSTRACT,
Line 4,

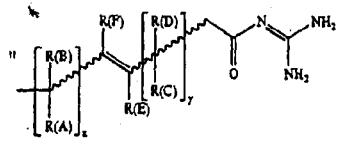 " should read -- 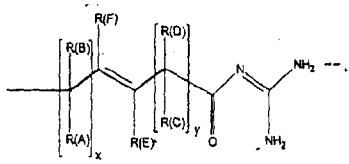 --.

Column 33,
Line 30, in the formula after "T is"

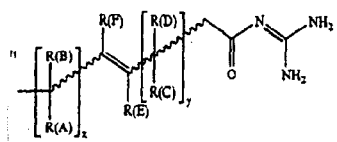 " should read -- 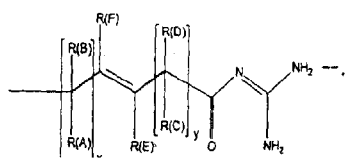 --.

Column 34,
Line 17, "—$SO_rR(17)_1$" should read -- —$So_rR(17)$ --

Column 36,
Line 25, in the formula after "T is"

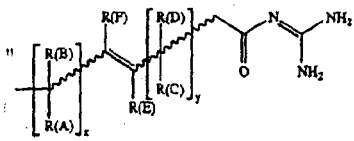 " should read -- 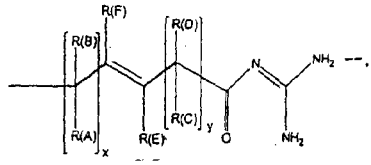 --.

UNITED STATES PATENT AND TRADEMARK OFFICE
CERTIFICATE OF CORRECTION

PATENT NO.   : 6,005,010
DATED        : December 21, 1999
INVENTOR(S)  : Schwark et al.

It is certified that error appears in the above-identified patent and that said Letters Patent is hereby corrected as shown below:

Column 37,
Line 37, "fmuoropropenoic" should read -- fluropropenoic --
Line 47, "dihydrochide" should read -- dihydrochloride --

Signed and Sealed this

Twenty-first Day of January, 2003

JAMES E. ROGAN
*Director of the United States Patent and Trademark Office*